US005606019A

United States Patent [19]
Cappello

[11] Patent Number: 5,606,019
[45] Date of Patent: Feb. 25, 1997

[54] SYNTHETIC PROTEIN AS IMPLANTABLES

[75] Inventor: Joseph Cappello, San Diego, Calif.

[73] Assignee: Protien Polymer Technologies, Inc., San Diego, Calif.

[21] Appl. No.: 212,237

[22] Filed: Mar. 11, 1994

Related U.S. Application Data

[63] Continuation-in-part of Ser. No. 609,716, Nov. 6, 1990, Pat. No. 5,514,581, and Ser. No. 53,049, Apr. 22, 1993, abandoned, which is a continuation-in-part of Ser. No. 114,618, Oct. 29, 1987, Pat. No. 5,243,038.

[51] Int. Cl.$^6$ .......................... C07K 7/06; A61K 38/00; A61K 38/17
[52] U.S. Cl. .................. 530/329; 435/69.1; 435/172.3; 435/273; 435/320.1; 530/353; 530/330
[58] Field of Search .................... 530/353, 329, 530/330; 435/69.1, 320.1, 122.3, 273; 623/11; 514/12

[56] References Cited

U.S. PATENT DOCUMENTS

| | | | |
|---|---|---|---|
| 4,215,200 | 7/1980 | Miyata et al. | 435/273 |
| 4,589,882 | 5/1986 | Urry | 528/328 |
| 5,243,038 | 9/1993 | Ferrari et al. | 536/23.1 |

OTHER PUBLICATIONS

Computerized Printout CA119:27323 (1995) of EP.488687 Reg. No's 151500–11–7 and 151500–12–8.
Brennan, "Fibrin Glue," Blood Reviews (1991) 5: 240–244.
Nissen et al., "Fibrin Glue in Otology and Neurotology," Am. J. of Otology (1993) 14: 147–150.
Francis & Marder, "Physiologic Regulation and Pathologic Disorders of Fibrinolysis," Human Pathology (1987) 18:263–274.
Frykman, "The Quest for Better Recovery from Peripheral Nerve Injury," J. of Hand Therapy (1993) Apr.–Jun. 1983–1988.
Greenberg et al., "Transglutaminases: Multifunctional Cross–Linking Enzymes that Stabilize Tissues," The FASEB Journal (1991) 5:3071–3077.
Rixon et al., "Nucleotide Sequence of the Gene for the y Chain of Human Fibrinogen," Biochemistry (1985) 24: 2077–2086.
Terris & Fee, "Current Issues in Nerve Repair," Arch Otolaryngol Head Neck Surg. (1993) 119: 725–731.

*Primary Examiner*—Herbert J. Lilling
*Attorney, Agent, or Firm*—Bertram I. Rowland

[57] ABSTRACT

Copolymers are provided having varying ratios of elastin and fibroin repeating units. By varying the length of segments of the elastin and fibroin repeating units, the absorption can be greatly varied. Tensile strengths remain relatively constant regardless of the composition within the prescribed ranges. The copolymer compositions and recombinant fibroin can be used for the production of a wide variety of formed objects and amorphous masses for use as implants.

4 Claims, No Drawings

SYNTHETIC PROTEIN AS IMPLANTABLES

CROSS REFERENCE TO RELATED APPLICATIONS

This application is a continuation-in-part of application Ser. Nos. 07/609,716, filed 6 Nov. 1990 now U.S. Pat. No. 5,514,581 and 08/053,049, filed 22 Apr. 1993, now abandoned which are a continuation-in-part of application Ser. No. 07/114,618, filed Oct. 29, 1987, now U.S. Pat. No. 5,243,038.

TECHNICAL FIELD

The field of this invention is the production and use of bioresorbable polypeptide polymers.

BACKGROUND

The rate at which an implanted material resorbs or biodegrades within the body can be a major factor in determining its utility as a biomaterial. So called inert materials, such as metals, ceramics and plastics have been shown to be useful for permanent implants. However, in applications in which a device serves as an aid to healing or as a temporary aid in surgical repair, a resorbable material has the advantage of not having to be removed, once healing has occurred. Resorbable sutures and staples, bone pins and screws, wound dressings, and injectable drug delivery systems or depots are examples of such devices. There are very few materials available today which have the physical, chemical and biological properties necessary for the fabrication of medical devices, which must degrade and resorb in the body without detrimental consequences.

Various synthetic organic polymers have found use, such as polylactides, polyglycolides, polyanhydrides and polyorthoesters, which degrade in the body by hydrolysis. Collagen, glycosaminoglycans and hyaluronic acid are examples of natural implantable materials which resorb at least partially by enzymatic degradation. The rates of resorption are limited to the nature of the particular material and modifications can change the rate of resorption, but at the same time may adversely affect the desired properties of the product.

Illustrative of efforts to vary resorption characteristics by compositional changes are synthetic resorbable sutures composed of copolymers of lactide and glycolide. By varying the ratio of lactic acid to glycolic acid, the rate of resorption may be varied. Unfortunately, rapidly resorbing compositions tend to be soft and weak. Slow resorbing compositions are stiff and strong. However, their resorption, which is hydrolytic, produces acid buffered by the tissue medium, where erosion occurs at the polymer surface. In addition, however, hydrolysis may occur internally, where the resulting acid catalyzes and accelerates the degradation of the polymer. Thus, internal pockets of degradation can lead to rapid and catastrophic failure of mechanical properties.

There is, therefore, a need for products which can be used in the production of implantable devices. Such products should have the desired mechanical properties of tensile strength, elasticity, formability, and the like, provide for controlled resorption, and be physiologically acceptable.
Relevant Literature U.S. Pat. No. 5,243,038 describes the preparation of high molecular weight, protein polymers and copolymers comprising long segments of small repeating units. Bioactive Polymeric Systems, Gebelein, C. G. and Carraher, C. E., eds., Plenum Press, New York, 1985; Contemporary Biomaterials, Boretos, John W. and Eden, Murray, eds., Noyes Publications, New Jersey, 1984; and Concise Guide to Biomedical Polymers: Their Design, Fabrication and Molding, Boretos, John W., Thomas pub., Illinois, 1973, describe compositions, characteristics, and applications of biomaterials.

SUMMARY OF THE INVENTION

Protein copolymers are provided having segments varying in the number of repetitive units, based on fibroin and elastin. The protein copolymers and silk homopolymers find use in the production of a wide variety of implantable devices and components thereof.

DESCRIPTION OF SPECIFIC EMBODIMENTS

Implantable devices and components thereof are provided comprised of recombinant novel copolymers having alternating segments of repetitive units based on fibroin (silk) in combination with elastin or recombinant polymers of fibroin. Particularly, the units for the most part are GAGAGS and VPGVG, respectively, although some variations are permitted, such as the particular order of the amino acids in the sequence and conservative substitutions, such as, but not limited to, replacing serine with threonine and glycine with alanine.

In the copolymers, by varying the ratio of the two different units, the length of the segments comprising each of the units, the molecular weight, any intervening sequences, modifications to the individual repeating units, and the like, one can vary the tensile properties of the product only moderately, such as elasticity, stiffness, hardness, ease of processing, and flexibility, while one can substantially vary the rate of resorption. Faster resorption can be achieved by reducing the number of repeating units of silk in the silk segment below about 8 units or increasing the number of elastin units per elastin segment to greater than 8, individually or in combination.

For the copolymers, the ratio of the average number of elastin units to the average number of silk units per segment of the repetitive units will be in the range of about 0.5, usually about 1–5. For the most part, there will be at least two fibroin units per segment and not more than about 12, usually not more than about ten, preferably ranging from about 2–8. For the elastin units, there will usually be at least two, more usually at least about four, generally ranging from about 6–32, more usually from about 6–18, preferably from about 6–16. The percent of amino acids contributed by the silk units will generally range from about 15–65%, more usually from about 15–60%, preferably about 20–55%.

The copolymers which find use in the invention will generally range from about 15–80% of amino acids provided by fibroin units, The polymers will be at least about 15 kDa and generally not more than about 150 kDa, usually not more than about 125 kDa, preferably ranging from about 35–100 kDa. In order to achieve the copolymers, the number of segments will provide for the desired molecular weight. Therefore, the number of segments can vary widely, depending upon the size of each individual segment. Thus, the number of segments may vary from about 2–40, more usually ranging from about 6–20.

Based on the method of preparation, there may be non-repetitive units at the N- and C- termini. Usually, the terminal sequences will contribute fewer than ten number percent of the amino acids, more usually fewer than five number percent of the amino acids. Generally, the sequence will range from about 0–125 amino acids, more usually from about 0–60 amino acids, where the total number of amino acids will generally not exceed about 100 amino acids, more usually not exceed about 50 amino acids.

For special applications the polymers may be modified by introducing intervening sequences between segments or blocks of segments, where the total number of repeating units per block may vary from about 4 to 40, thus involving two or more segments. The intervening sequences may include from about 1 to 60, usually about 3 to 40 amino acids, and may provide for a wide variety of properties. For example, by including amino acids which have chemically reactive sidechains, one may provide for sites for linking a variety of chemically or physiologically active compounds, for cross-linking, for covalently bonding compound which may change the rate of resorption, tensile properties or the like. Thus amino acids, such as cysteine, aspartic acid, glutamic acid, lysine and arginine may be incorporated in these intervening sequences. Alternatively, the sequence may provide for sequences which have physiological activity, such as cell binding, specific protein binding, enzyme substrates, specific receptor binding, and the like. In this manner, the useful properties of the basic protein may be greatly varied in accordance with the intended use, being tailored for specific applications.

The polymers have good mechanical properties to form a wide variety of products. The protein polymers may be drawn, molded, cast, spun, extruded, or the like, in accordance with known ways for forming structures such as films, formed objects, fibers, or unformed structures, such as amorphous masses, and the like. Also, gels may be formed which may be shaped in a variety of ways, depending upon the particular application. The compositions can be sterilized by conventional ways to provide sterile products.

The subject compositions can be used to provide a wide variety of devices, such as membranes, sutures, staples, bone pins, screws, wound dressings, and as drug depots, where the products may be formed prior to implantation or in situ. The compositions as formed are found to provide the necessary mechanical properties for the particular applications, the resorption times can be controlled so as to ensure mechanical maintenance during the time required for structure integrity, and at the same time ensuring that the device or material need not be manually removed, since the material undergoes resorption.

The subject compositions may be used in combination with other materials, such as collagen, fibrinogen, and other natural proteins; hyaluronic acid, dextran, or other polysaccharides; or polyethylene oxide, polyhydroxyalkanoates, or other polyesters, to produce blended materials to provide a larger range of physical and biological properties, for applications, such as wound dressings or membranes for the prevention of surgical adhesions. For example, the protein polymer SELP3 combined with sodium hyaluronate, in equal proportions by weight, may be used to prepare a film, which compared to pure hyaluronate gels, exhibits greater mechanical toughness and a decreased resorption rate.

The compositions may be prepared in accordance with the manner described in U.S. Pat. No. 5,243,038. This procedure involves synthesizing small segments of single stranded DNA of from about 15–150 nucleotides to provide a plurality of fragments which have cohesive ends, which may be ligated together to form a segment or a plurality of segments. The first dsDNA fragment is cloned to ensure the appropriate sequence, followed by the addition of successive fragments, which are in turn cloned and characterized, to ensure that the integrity of the sequence is retained. The fragments are joined together to form a "monomer" which then becomes the major repeating building block of the polymer gene.

Alternatively, long single strands may be prepared, cloned and characterized, generally being of at least 100 nucleotides and up to about 300 nucleotides, where the two single strands are hybridized, cloned and characterized and may then serve as the monomer or the building block. The monomers may then be multimerized, having complementary termini, particularly cohesive ends, so that the polymers will have two or more monomers present. The multimers may then be cloned in an appropriate vector and characterized to determine the number of monomers and the desired size polymer selected. Expression can be achieved in an expression host using transcriptional regulatory regions functional in the expression host. The expression host can be prokaryotic or eukaryotic, particularly bacterial, e.g. *E. coli, B. subtills*, etc.; yeast, e.g. Saccharomyces, Neurospora, etc.; insect cells, plant cells, and the like. If desired, a signal sequence may be provided for secretion of the polymer. A wide variety of signal sequences are known and have been used extensively for secreting proteins which are not normally secreted by the expression host.

After completion of expression, where the protein is retained in the host, the cells are disrupted and the product extracted from the lysate. Where the product is secreted, the product may be isolated from the supernatant. In either case, various techniques for purifying the products may be employed, depending upon whether the products are soluble or insoluble in the medium. Where insoluble, impurities may be extracted from the polymer, leaving the polymer intact. Where soluble, the polymer may be purified in accordance with conventional ways, such as extraction, chromatography, or the like.

The following examples are offered by way of illustration and not by limitation.

EXPERIMENTAL

EXAMPLE 1.

Preparation of polymers.

*E. coli* strain EC3 containing the respective plasmid encoding each polymer shown in Table 1 below, was prepared in accordance with the methods described in U.S. Pat. No. 5,243,038. Each strain was then fermented using a fed-batch method.

Biomass for each polymer was harvested from the fermentation broth by centrifugation in a Sorval RC3B using a H6000A rotor at 5,000 rpm for 30 minutes at 10° C. to yield a packed cell paste. 500 grams of cell paste was resuspended in 2 liters of 50 mM Tris buffer (pH=8.0). The cell slurry was homogenized using a Manton Gaulin cell disrupter at 7–8,000 psi with three complete passes of the liquid. The cell homogenate was passed through a chilled heat exchanger to maintain the temperature at 15° C. or less. Pancreatic DNAse was added to the homogenate to a final concentration of 1 µg/ml and stirred at room temperature for 2 hours. The homogenate was centrifuged in a Sorval RC3B centrifuge using a H6000A rotor at 5,000 rpm for 1 hour at 10° C.

For SELP0, 3, 7, and 8, the supernatant was placed into 12–14,000 molecular weight cut-off dialysis bags and dialyzed against 2 changes of 100×volume of 20 mM sodium acetate buffer (pH=4.7) for 24 hours. The contents of the bags were transferred to centrifuge bottles and centrifuged in a Sorval RC3B centrifuge using a H6000A rotor at 5,000 rpm for 1 hour at 10° C. The supernatant was removed to a large beaker and the pH adjusted to 8.0 by addition of 30% ammonium hydroxide. Saturated ammonium sulfate was then added to reach a final concentration of 20% for SELP0, 25% for SELP8 and 3, and 33% for SELP7. The solution was stirred at room temperature for 1 hour. The solution was centrifuged in a Sorval RC3B using a H6000A rotor at 5,000 rpm for 30 minutes at 10° C. The pellet was resuspended in 2 liters of deionized water, placed in dialysis bags, and dialyzed against 3 changes of deionized water of 100× volume over 48 hours. The contents of the bags were shell frozen and lyophilized to dryness.

For SELP4 and 5, the centrifuged homogenate supernatant was directly precipitated with ammonium sulfate at a concentration of 25%. The solution was then centrifuged in a Sorval RC3B using a H6000A rotor at 5,000 rpm for 1 hour at 10° C. The pellet was resuspended in 5 liters of 4M LiBr and stirred at 4° C. for 16 hours. The solution was centrifuged in a Sorval RC3B centrifuge using a H6000A rotor at 5,000 rpm at 10° C. for 1 hour. The pH of the supernatant was adjusted to pH 3.7 by slow addition of 1M acetic acid at 4° C. The solution was centrifuged in a Sorval RC3B using a H6000A rotor at 5,000 rpm at 10° C. for 1 hour. The supernatant pH was adjusted to 8.0 by addition of ammonium hydroxide and then dialyzed against 3 changes of 100×volume deionized water over 48 hours. The solution was removed from dialysis and centrifuged in a Sorval RC3B using a H6000A rotor at 5,000 rpm at 10° C. for 1 hour. Saturated ammonium sulfate was added to the supernatant to reach 25% of saturation and stirred for 1 hour. The solution was centrifuged in a Sorval RC3B using a H6000A rotor at 5,000 rpm at 10° C. for 1 hour. The pellet was dissolved in 4.5M LiBr, placed in dialysis bags, and dialyzed against 3 changes of 100×volume of deionized water. The contents of the bags were shell frozen and lyophilized to dryness.

All reagent solutions used in the following procedures were depyrogenated prior to use by filtration through a 10,000 nominal molecular weight cut-off hollow fiber cartridge (AG Technologies). All glassware and utensils used were sterilized and depyrogenated by heating at 180° C. for 4 hours. 4–5 grams of all SELP dried polymers were dissolved in 1.2 liters of 10M urea. 20 mls of 2M Tris pH 8.0 and 780 mls of milli-Q water were added. The solution was sonicated to promote full dissolution of the protein. 500 grams of Whatman DE52 ion exchange resin was prepared by precycling through acid and base treatment as recommended by manufacturer prior to and in between each usage. The resin was finally equilibrated with 6M urea, 20 mM Tris pH 8.0 in a beaker with gentle stirring. The resin was filtered in a buchner funnel until excessive liquid was removed. The cake of resin was placed in a beaker and the protein solution was added. The slurry was stirred gently for 1 hour. The slurry was filtered in a buchner funnel and the liquid was collected in a cleaned vacuum flask. 500 grams of fresh precycled and equilibrated resin was added to a clean beaker and the filtered solution was added. The slurry was stirred gently for 1 hour and filtered again. The filtered solution was once more combined with 500 grams of freshly precycled and equilibrated resin, stirred for 1 hour, and filtered. The final filtered solution was placed in 6,000 molecular weight cut-off dialysis bags which had been soaked in 0.5N NaOH for at least 24 hours. The solution was dialyzed against 3 changes of 100×volume of deionized water. The dialyzed solution was removed from the bags, placed in depyrogenated lyophilization flasks and lyophilized to dryness. Employing the above procedure, the following polymers were prepared.

TABLE 1

| Polymer (MW) | Polymer Block Sequence[1] | Domain Abbr.[2] | E/S[3] | %S[4] |
|---|---|---|---|---|
| SELP0 (80,502) | [(VPGVG)$_8$(GAGAGS)$_2$]$_{18}$ (SEQ ID NO: 03) | E8S2 | 4.0 | 21.9 |
| SELP8 (69,934) | [(VPGVG)$_8$(GAGAGS)$_4$]$_{13}$ (SEQ ID NO: 04) | E8S4 | 2.0 | 35.3 |
| SELP7 (80,338) | [(VPGVG)$_8$(GAGAGS)$_6$]$_{13}$ (SEQ ID NO: 05) | E8S6 | 1.33 | 45.0 |
| SELP3 (84,267) | [(VPGVG)$_8$(GAGAGS)$_8$]$_{12}$ (SEQ ID NO: 06) | E8S8 | 1.0 | 51.9 |
| SELP4 (79,574) | [(VPGVG)$_{12}$(GAGAGS)$_8$]$_9$ (SEQ ID NO: 07) | E12S8 | 1.5 | 42.2 |
| SELP5 (84,557) | [(VPGVG)$_{16}$(GAGAGS)$_8$]$_8$ (SEQ ID NO: 08) | E16S8 | 2.0 | 35.7 |

[1]The first and last block domain of each polymer is split within the silk blocks such that both parts sum to a whole domain. All polymers also contain an additional head and tail sequence which constitutes approximately 6% of the total amino acids.
[2]Designates the number of consecutive blocks per repeating domain (E = elastin-like block, S = silk-like block)
[3]Ratio of blocks per polymer.
[4]% of total amino acids in polymer contributed by silk-like blocks.

Other polymers which were prepared include [(VPGVG)$_{32}$(GAGAGS)$_8$] (SEQ. ID NO:09), referred to as SELP6

EXAMPLE 2.

SELP films.
SELP films that were approximately 0.05 mm thickness were produced by solvent evaporation.

Approximately 1.7 grams of each polymer, except for SELP7 where only 1.05 grams was used, were solubilized in 34 mls of 88% formic acid. The solution was stirred for 7 hours at room temperature to insure complete solubilization. The solution was then poured into a film casting apparatus consisting essentially of a rectangular polyethylene trough with a removable polyethylene bottom. The casting apparatus was placed in a vacuum oven attached to a nitrogen gas source for sparging the atmosphere. The films were dried in the sealed oven drawing a 10–15 micron vacuum with a slow continual influx of nitrogen gas at 60°–75° C. After 15–18 hours of drying, the apparatus was disassembled and the film was peeled off the polyethylene bottom. The films were exposed for 5 minutes to a basic atmosphere (5% open solution of ammonium hydroxide in a sealed desiccator) to neutralize any residual formic acid.

A polyethylene sheet of the same area dimensions as the protein film was roughened by hand using fine grit sand paper and a fine film of cyanoacrylate glue was spread over its surface. The protein film was applied to the wet surface. A teflon sheet was placed on top and bottom of the polyethylene and protein layers and stainless steel plates were placed around those. The entire assembly was pressed in a Carver laboratory press at a force of 0.8 metric tons for 18 hours at room temperature. The polyethylene/protein film laminated sheet was placed on a cutting board and 1.3 cm diameter discs were punched out using a stainless steel punch and rubber mallet. The discs were placed individually in stoppered glass vials.

Specimens were produced from each of the polymers as well as denatured collagen protein (DCP) produced identically as described for the SELP films. Bovine collagen (fibrillar form, lot number 921101) was obtained from Colla-Tec, Inc. (Plainsboro, N.J.). It was completely solubilized in 88% formic acid producing a clear but viscous solution. All specimens were sterilized by electron beam irradiation at 2.5±0.2 Mrads. Each disk was implanted subcutaneously in the back of rats such that the protein film was in direct contact with the muscle tissue. The specimens remained in the animals for different periods of time: one, four and seven weeks post implantation. At each time interval six specimens per polymer group were retrieved for protein analysis. Additional specimens from each group were evaluated for tissue reaction by histology.

Non-implanted and retrieved specimens were analyzed to determine the mass of SELP film contained per specimen. Amino acid analysis was performed on each specimen by sealing them individually in an hydrolysis vial with constant boiling hydrochloric acid and heating for 24 hr at 100°–110° C. After hydrolysis, the specimen was extracted and an aliquot of the extract was derivatized with PTC. The derivatized amino acids were separated by reverse phase HPLC and quantified by their absorbance at 254 nm according to the methods of Henrickson and Meredith (*Anal Biochem.* 137, 65–74, 1984).

The mass of the SELP film present on each specimen was determined. The amino acid contribution of the SELP protein was estimated based on the total content of the amino acids G,A,S,V and P which for the pure polymers is>95%. Other amino acids potentially contributed by extraneous protein deposited onto the specimens during residence in the body were excluded from these analyses. Average SELP film mass for non-implanted specimens was determined from the same batch of specimens used for implantation. Average SELP film mass for retrieved specimens was similarly calculated except that replicates having values greater than two standard deviations from the mean were discarded. Deviations in many cases were due to partial retrieval of specimens that had fragmented in the tissue after implantation and may not reflect true resorption. Resorption Analysis and Results Resorption analysis was conducted statistically by analyzing four specimen population treatment groups. These were: (1) non-implanted; (2) one week post-implantation; (3) four weeks post-implantation; and (4) seven weeks post-implantation.

TABLE 2

Polymer Film Mass Remaining as Determined by AA Composition Analysis (in milligrams)

|  | SELP0 |  | SELP3 |  | SELP4 |  | SELP5 |  |
|---|---|---|---|---|---|---|---|---|
| Initial Film Mass | 12.21 | +/−1.41 | 5.99 | +/−0.46 | 8.19 | +/−0.86 | 8.51 | +/−1.04 |
| 1 Week Film Mass | 0.53 | +/−0.31 | 5.93 | +/−0.73 | 7.89 | +/−0.55 | 7.72 | +/−1.57 |
| 4 Week Film Mass | 0.27 | +/−0.13 | 6.24 | +/−0.61 | 9.20 | +/−1.08 | 7.49 | +/−0.75 |
| 7 Week Film Mass | 0.10 | +/−0.02 | 3.49 | +/−1.60 | 8.56 | +/−0.67 | 9.77 | +/−0.97 |

|  | SELP7 |  | SELP8 |  | DCP |  |
|---|---|---|---|---|---|---|
| Initial Film Mass | 3.27 | +/−0.34 | 8.43 | +/−0.59 | 6.6 | +/−1.04 |
| 1 Week Film Mass | 4.67 | +/−1.33 | 11.13 | +/−1.40 | 0.15 | +/−0.07 |
| 4 Week Film Mass | 0.19 | +/−0.16 | 8.26 | +/−1.21 | 0.09 | +/−0.03 |
| 7 Week Film Mass | 0.08 | +/−0.03 | 1.52 | +/−1.40 | 0.07 | +/−0.03 |

TABLE 3

Polymer Film Remaining as Percent of Non-implanted Mass

|  | SELP0 | SELP3 | SELP4 | SELP5 | SELP7 | SELP8 | DCP |
|---|---|---|---|---|---|---|---|
| Initial film Mass | 100.0% | 100.0% | 100.0% | 100.0% | 100.0% | 100.0% | 100.0% |
| 1 Week Film Mass | 4.3% | 98.9% | 96.3% | 90.7% | 142.8% | 132.0% | 2.3% |

TABLE 3-continued

| | Polymer Film Remaining as Percent of Non-implanted Mass | | | | | | |
|---|---|---|---|---|---|---|---|
| | SELP0 | SELP3 | SELP4 | SELP5 | SELP7 | SELP8 | DCP |
| 4 Week Film Mass | 2.2% | 104.1% | 112.4% | 88.0% | 5.8% | 98.0% | 1.3% |
| 7 Week Film Mass | 0.8% | 58.2% | 104.5% | 103.1% | 2.6% | 18.1% | 1.1% |

The results from Table 2 are the values for the mass of protein film contained on specimens after implantation. Each value is the mean of at least five specimen masses as determined by amino acid composition. Table 3 displays the same values as a percent of the initial weight prior to implantation as determined by the mean mass of six specimens of the non-implanted specimens. The results indicate that upon implantation, SELP0 and DCP are substantially resorbed by one week, falling below 5% of their non-implanted masses. SELP7 is substantially resorbed by four weeks with only 5.8% remaining. SELP8 and SELP3 are resorbing by seven weeks with mean values of 18.1% and 58.2% remaining, respectively. SELP4 and SELP5 films show no evidence of resorption at seven weeks.

From the above results one may conclude the following. Faster resorption correlates with compositions containing domains of silk-like blocks fewer than eight. The polymers containing eight silk-like blocks have substantially reduced rates of resorption. However, the total content of silk-like blocks in the copolymer composition does not correlate with resorption rate. While very similar compositionally, SELP7 and SELP8 resorbed quickly, while SELP4 and SELP5 do not resorb in seven weeks. The lack of resorption of SELP4 and SELP5 films at seven weeks post-implantation corresponds with repeating domains containing greater than eight elastin-like blocks. Although their silk-like block lengths are identical at eight, SELP4 and 5 with elastin-like block lengths of 12 and 16 resorb to a lesser degree than SELP3, which has an elastin-like block length of 8.

The subject polymers, regardless of their composition, form free-standing films with strength enough to allow easy handling. SELP7 and SELP4 films have tensile strengths of 19±1 and 21±8 MPa, respectively. The compositional difference between them that causes SELP7 to resorb in four weeks and SELP4 to remain intact beyond seven weeks makes little apparent difference in their tensile properties. These strengths are adequate for their use in surgical and wound healing applications.

The observed resorption of these polymers occurs via surface erosion. This is consistent with the mechanism of degradation of SELP proteins within the body. At physiological conditions, proteins will degrade only through the action of proteases. Because endogenous proteases are high molecular weight compounds of approximately 20 kDa or greater, their diffusion into the dense SELP films will be limited. The degradation of SELP films is, therefore, progressive from the external surfaces of the material. The subject materials therefore should undergo a slow loss of mechanical integrity while being reduced in mass.

It is evident from the above results, that the subject compositions have particularly desirable properties for uses in implants. By varying compositional ratios, the rate of resorption can be varied greatly, without significant changes in tensile properties. The compositions can be formed in a wide variety of devices or objects, to find extensive use for a variety of purposes and context as implants.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A protein polymer of at least 15 kD and comprising alternating blocks of two units each of VPGVG (SEQ ID NO: 02) and GAGAGS (SEG ID NO: 01), wherein at least 15 to 80% of amino acids of said alternating blocks of said protein polymer are present as GAGAGS units.

2. A protein polymer according to claim 1, wherein blocks of VPGVG (SEQ ID NO:02) have from two to thirty-two units and blocks of GAGAGS (SEQ ID NO:02) have from two to twelve units.

3. A protein polymer according to claim 2, wherein said blocks of VPGVG (SEQ ID NO:02) have from eight to twenty units.

4. A protein polymer according to claim 1, wherein said protein polymer has blocks of VPGVG (SEQ ID NO:02) and GAGAGS (SEQ ID NO:01) with unit ratios of: 8:2; 8:4; 8:6; 12:8; 16:8; and 32:8.

* * * * *

UNITED STATES PATENT AND TRADEMARK OFFICE
CERTIFICATE OF CORRECTION

PATENT NO. : 5,606,019

DATED : February 25, 1997

INVENTOR(S) : Capello

It is certified that error appears in the above-indentified patent and that said Letters Patent is hereby corrected as shown below:

On the cover sheet, at [73] Assignee, delete "Protien" and insert therefor --Protein--.

Signed and Sealed this

Third Day of February, 1998

Attest:

BRUCE LEHMAN

*Attesting Officer*    *Commissioner of Patents and Trademarks*

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
      ( A ) LENGTH: 6 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:1:

Gly Ala Gly Ala Gly Ser (2) INFORMATION FOR SEQ ID NO:2:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

```
Val  Pro  Gly  Val  Gly
 1               5
```

(2) INFORMATION FOR SEQ ID NO:3:

(i) SEQUENCE CHARACTERISTICS:
        (A) LENGTH: 936 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

```
Val  Pro  Gly  Val  Gly  Val  Pro  Gly  Val  Gly  Val  Pro  Gly  Val  Gly  Val
 1                5                   10                  15
Pro  Gly  Val  Gly  Val  Pro  Gly  Val  Gly  Val  Pro  Gly  Val  Gly  Val  Pro
                20                  25                  30
Gly  Val  Gly  Val  Pro  Gly  Val  Gly  Gly  Ala  Gly  Ala  Gly  Ser  Gly  Ala
                35                  40                  45
Gly  Ala  Gly  Ser  Val  Pro  Gly  Val  Gly  Val  Pro  Gly  Val  Gly  Val  Pro
                50                  55                  60
Gly  Val  Gly  Val  Pro  Gly  Val  Gly  Val  Pro  Gly  Val  Gly  Val  Pro  Gly
 65                 70                  75                      80
Val  Gly  Val  Pro  Gly  Val  Gly  Val  Pro  Gly  Val  Gly  Gly  Ala  Gly  Ala
                85                  90                  95
Gly  Ser  Gly  Ala  Gly  Ala  Gly  Ser  Val  Pro  Gly  Val  Gly  Val  Pro  Gly
               100                 105                 110
Val  Gly  Val  Pro  Gly  Val  Gly  Val  Pro  Gly  Val  Gly  Val  Pro  Gly  Val
               115                 120                 125
Gly  Val  Pro  Gly  Val  Gly  Val  Pro  Gly  Val  Gly  Val  Pro  Gly  Val  Gly
               130                 135                 140
Gly  Ala  Gly  Ala  Gly  Ser  Gly  Ala  Gly  Ala  Gly  Ser  Val  Pro  Gly  Val
 145                150                 155                     160
Gly  Val  Pro  Gly  Val  Gly  Val  Pro  Gly  Val  Gly  Val  Pro  Gly  Val  Gly
                165                 170                 175
Val  Pro  Gly  Val  Gly  Val  Pro  Gly  Val  Gly  Val  Pro  Gly  Val  Gly  Val
                180                 185                 190
Pro  Gly  Val  Gly  Gly  Ala  Gly  Ala  Gly  Ser  Gly  Ala  Gly  Ala  Gly  Ser
                195                 200                 205
Val  Pro  Gly  Val  Gly  Val  Pro  Gly  Val  Gly  Val  Pro  Gly  Val  Gly  Val
                210                 215                 220
Pro  Gly  Val  Gly  Val  Pro  Gly  Val  Gly  Val  Pro  Gly  Val  Gly  Val  Pro
 225                230                 235                     240
Gly  Val  Gly  Val  Pro  Gly  Val  Gly  Gly  Ala  Gly  Ala  Gly  Ser  Gly  Ala
                245                 250                 255
Gly  Ala  Gly  Ser  Val  Pro  Gly  Val  Gly  Val  Pro  Gly  Val  Gly  Val  Pro
```

-continued

|   |   |   |   |   | 260 |   |   |   |   | 265 |   |   |   |   | 270 |   |   |
|---|---|---|---|---|---|---|---|---|---|---|---|---|---|---|---|---|---|
| Gly | Val | Gly | Val | Pro | Gly | Val | Gly | Val | Pro | Gly | Val | Gly | Val | Pro | Gly |
|  |  | 275 |  |  |  |  | 280 |  |  |  |  | 285 |  |  |  |
| Val | Gly | Val | Pro | Gly | Val | Gly | Val | Pro | Gly | Val | Gly | Gly | Ala | Gly | Ala |
|  |  | 290 |  |  |  |  | 295 |  |  |  |  | 300 |  |  |  |
| Gly | Ser | Gly | Ala | Gly | Ala | Gly | Ser | Val | Pro | Gly | Val | Gly | Val | Pro | Gly |
| 305 |  |  |  |  | 310 |  |  |  |  | 315 |  |  |  |  | 320 |
| Val | Gly | Val | Pro | Gly | Val | Gly | Val | Pro | Gly | Val | Gly | Val | Pro | Gly | Val |
|  |  |  |  | 325 |  |  |  |  | 330 |  |  |  |  | 335 |  |
| Gly | Val | Pro | Gly | Val | Gly | Val | Pro | Gly | Val | Gly | Val | Pro | Gly | Val | Gly |
|  |  |  | 340 |  |  |  |  | 345 |  |  |  |  | 350 |  |  |
| Gly | Ala | Gly | Ala | Gly | Ser | Gly | Ala | Gly | Ala | Gly | Ser | Val | Pro | Gly | Val |
|  |  | 355 |  |  |  |  | 360 |  |  |  |  | 365 |  |  |  |
| Gly | Val | Pro | Gly | Val | Gly | Val | Pro | Gly | Val | Gly | Val | Pro | Gly | Val | Gly |
|  |  | 370 |  |  |  |  | 375 |  |  |  |  | 380 |  |  |  |
| Val | Pro | Gly | Val | Gly | Val | Pro | Gly | Val | Gly | Val | Pro | Gly | Val | Gly | Val |
| 385 |  |  |  |  |  | 390 |  |  |  |  | 395 |  |  |  |  | 400 |
| Pro | Gly | Val | Gly | Gly | Ala | Gly | Ala | Gly | Ser | Gly | Ala | Gly | Ala | Gly | Ser |
|  |  |  |  | 405 |  |  |  |  | 410 |  |  |  |  | 415 |  |
| Val | Pro | Gly | Val | Gly | Val | Pro | Gly | Val | Gly | Val | Pro | Gly | Val | Gly | Val |
|  |  |  | 420 |  |  |  |  | 425 |  |  |  |  | 430 |  |  |
| Pro | Gly | Val | Gly | Val | Pro | Gly | Val | Gly | Val | Pro | Gly | Val | Gly | Val | Pro |
|  |  | 435 |  |  |  |  | 440 |  |  |  |  | 445 |  |  |  |
| Gly | Val | Gly | Val | Pro | Gly | Val | Gly | Gly | Ala | Gly | Ala | Gly | Ser | Gly | Ala |
| 450 |  |  |  |  | 455 |  |  |  |  | 460 |  |  |  |  |  |
| Gly | Ala | Gly | Ser | Val | Pro | Gly | Val | Gly | Val | Pro | Gly | Val | Gly | Val | Pro |
| 465 |  |  |  |  | 470 |  |  |  |  | 475 |  |  |  |  | 480 |
| Gly | Val | Gly | Val | Pro | Gly | Val | Gly | Val | Pro | Gly | Val | Gly | Val | Pro | Gly |
|  |  |  |  | 485 |  |  |  |  | 490 |  |  |  |  | 495 |  |
| Val | Gly | Val | Pro | Gly | Val | Gly | Val | Pro | Gly | Val | Gly | Gly | Ala | Gly | Ala |
|  |  |  | 500 |  |  |  |  | 505 |  |  |  |  | 510 |  |  |
| Gly | Ser | Gly | Ala | Gly | Ala | Gly | Ser | Val | Pro | Gly | Val | Gly | Val | Pro | Gly |
|  |  | 515 |  |  |  |  | 520 |  |  |  |  | 525 |  |  |  |
| Val | Gly | Val | Pro | Gly | Val | Gly | Val | Pro | Gly | Val | Gly | Val | Pro | Gly | Val |
|  |  | 530 |  |  |  |  | 535 |  |  |  |  | 540 |  |  |  |
| Gly | Val | Pro | Gly | Val | Gly | Val | Pro | Gly | Val | Gly | Val | Pro | Gly | Val | Gly |
| 545 |  |  |  |  | 550 |  |  |  |  | 555 |  |  |  |  | 560 |
| Gly | Ala | Gly | Ala | Gly | Ser | Gly | Ala | Gly | Ala | Gly | Ser | Val | Pro | Gly | Val |
|  |  |  |  | 565 |  |  |  |  | 570 |  |  |  |  | 575 |  |
| Gly | Val | Pro | Gly | Val | Gly | Val | Pro | Gly | Val | Gly | Val | Pro | Gly | Val | Gly |
|  |  |  | 580 |  |  |  |  | 585 |  |  |  |  | 590 |  |  |
| Val | Pro | Gly | Val | Gly | Val | Pro | Gly | Val | Gly | Val | Pro | Gly | Val | Gly | Val |
|  |  | 595 |  |  |  |  | 600 |  |  |  |  | 605 |  |  |  |
| Pro | Gly | Val | Gly | Gly | Ala | Gly | Ala | Gly | Ser | Gly | Ala | Gly | Ala | Gly | Ser |
|  |  | 610 |  |  |  |  | 615 |  |  |  |  | 620 |  |  |  |
| Val | Pro | Gly | Val | Gly | Val | Pro | Gly | Val | Gly | Val | Pro | Gly | Val | Gly | Val |
| 625 |  |  |  |  |  | 630 |  |  |  |  | 635 |  |  |  |  | 640 |
| Pro | Gly | Val | Gly | Val | Pro | Gly | Val | Gly | Val | Pro | Gly | Val | Gly | Val | Pro |
|  |  |  |  | 645 |  |  |  |  | 650 |  |  |  |  | 655 |  |
| Gly | Val | Gly | Val | Pro | Gly | Val | Gly | Gly | Ala | Gly | Ala | Gly | Ser | Gly | Ala |
|  |  |  |  | 660 |  |  |  |  | 665 |  |  |  |  | 670 |  |
| Gly | Ala | Gly | Ser | Val | Pro | Gly | Val | Gly | Val | Pro | Gly | Val | Gly | Val | Pro |
|  |  | 675 |  |  |  |  | 680 |  |  |  |  | 685 |  |  |  |

```
Gly  Val  Gly  Val  Pro  Gly  Val  Gly  Val  Pro  Gly  Val  Gly  Val  Pro  Gly
     690                      695                      700
Val  Gly  Val  Pro  Gly  Val  Gly  Val  Pro  Gly  Val  Gly  Gly  Ala  Gly  Ala
705                      710                      715                      720
Gly  Ser  Gly  Ala  Gly  Ala  Gly  Ser  Val  Pro  Gly  Val  Gly  Val  Pro  Gly
               725                      730                      735
Val  Gly  Val  Pro  Gly  Val  Gly  Val  Pro  Gly  Val  Gly  Val  Pro  Gly  Val
               740                      745                      750
Gly  Val  Pro  Gly  Val  Gly  Val  Pro  Gly  Val  Gly  Val  Pro  Gly  Val  Gly
          755                      760                      765
Gly  Ala  Gly  Ala  Gly  Ser  Gly  Ala  Gly  Ala  Gly  Ser  Val  Pro  Gly  Val
     770                      775                      780
Gly  Val  Pro  Gly  Val  Gly  Val  Pro  Gly  Val  Gly  Val  Pro  Gly  Val  Gly
785                      790                      795                      800
Val  Pro  Gly  Val  Gly  Val  Pro  Gly  Val  Gly  Val  Pro  Gly  Val  Gly  Val
                    805                      810                      815
Pro  Gly  Val  Gly  Gly  Ala  Gly  Ala  Gly  Ser  Gly  Ala  Gly  Ala  Gly  Ser
               820                      825                      830
Val  Pro  Gly  Val  Gly  Val  Pro  Gly  Val  Gly  Val  Pro  Gly  Val  Gly  Val
               835                      840                      845
Pro  Gly  Val  Gly  Val  Pro  Gly  Val  Gly  Val  Pro  Gly  Val  Gly  Val  Pro
     850                      855                      860
Gly  Val  Gly  Val  Pro  Gly  Val  Gly  Gly  Ala  Gly  Ala  Gly  Ser  Gly  Ala
865                      870                      875                      880
Gly  Ala  Gly  Ser  Val  Pro  Gly  Val  Gly  Val  Pro  Gly  Val  Gly  Val  Pro
               885                      890                      895
Gly  Val  Gly. Val  Pro  Gly  Val  Gly  Val  Pro  Gly  Val  Gly  Val  Pro  Gly
               900                      905                      910
Val  Gly  Val  Pro  Gly  Val  Gly  Val  Pro  Gly  Val  Gly  Gly  Ala  Gly  Ala
          915                      920                      925
Gly  Ser  Gly  Ala  Gly  Ala  Gly  Ser
     930                      935
```

( 2 ) INFORMATION FOR SEQ ID NO:4:

( i ) SEQUENCE CHARACTERISTICS:
        ( A ) LENGTH: 832 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:4:

```
Val  Pro  Gly  Val  Gly  Val  Pro  Gly  Val  Gly  Val  Pro  Gly  Val  Gly  Val
1                        5                        10                       15
Pro  Gly  Val  Gly  Val  Pro  Gly  Val  Gly  Val  Pro  Gly  Val  Gly  Val  Pro
               20                       25                       30
Gly  Val  Gly  Val  Pro  Gly  Val  Gly  Gly  Ala  Gly  Ala  Gly  Ser  Gly  Ala
          35                       40                       45
Gly  Ala  Gly  Ser  Gly  Ala  Gly  Ala  Gly  Ser  Gly  Ala  Gly  Ala  Gly  Ser
     50                       55                       60
Val  Pro  Gly  Val  Gly  Val  Pro  Gly  Val  Gly  Val  Pro  Gly  Val  Gly  Val
65                       70                       75                       80
Pro  Gly  Val  Gly  Val  Pro  Gly  Val  Gly  Val  Pro  Gly  Val  Gly  Val  Pro
               85                       90                       95
Gly  Val  Gly  Val  Pro  Gly  Val  Gly  Gly  Ala  Gly  Ala  Gly  Ser  Gly  Ala
```

-continued

|   |   |   | 100 |   |   |   | 105 |   |   |   | 110 |   |   |
|---|---|---|---|---|---|---|---|---|---|---|---|---|---|
| Gly | Ala | Gly | Ser | Gly | Ala | Gly | Ala | Gly | Ser | Gly | Ala | Gly | Ser |
|   |   | 115 |   |   |   | 120 |   |   |   | 125 |   |   |   |
| Val | Pro | Gly | Val | Gly | Val | Pro | Gly | Val | Gly | Val | Pro | Gly | Val | Gly | Val |
|   |   | 130 |   |   |   | 135 |   |   |   | 140 |   |   |   |
| Pro | Gly | Val | Gly | Val | Pro | Gly | Val | Gly | Val | Pro | Gly | Val | Gly | Val | Pro |
| 145 |   |   |   |   | 150 |   |   |   |   | 155 |   |   |   |   | 160 |
| Gly | Val | Gly | Val | Pro | Gly | Val | Gly | Gly | Ala | Gly | Ala | Gly | Ser | Gly | Ala |
|   |   |   |   | 165 |   |   |   |   | 170 |   |   |   |   | 175 |   |
| Gly | Ala | Gly | Ser | Gly | Ala | Gly | Ala | Gly | Ser | Gly | Ala | Gly | Ala | Gly | Ser |
|   |   |   | 180 |   |   |   |   | 185 |   |   |   |   | 190 |   |   |
| Val | Pro | Gly | Val | Gly | Val | Pro | Gly | Val | Gly | Val | Pro | Gly | Val | Gly | Val |
|   |   |   | 195 |   |   |   |   | 200 |   |   |   |   | 205 |   |   |
| Pro | Gly | Val | Gly | Val | Pro | Gly | Val | Gly | Val | Pro | Gly | Val | Gly | Val | Pro |
|   | 210 |   |   |   |   | 215 |   |   |   |   | 220 |   |   |   |   |
| Gly | Val | Gly | Val | Pro | Gly | Val | Gly | Gly | Ala | Gly | Ala | Gly | Ser | Gly | Ala |
| 225 |   |   |   |   | 230 |   |   |   |   | 235 |   |   |   |   | 240 |
| Gly | Ala | Gly | Ser | Gly | Ala | Gly | Ala | Gly | Ser | Gly | Ala | Gly | Ala | Gly | Ser |
|   |   |   | 245 |   |   |   |   | 250 |   |   |   |   | 255 |   |   |
| Val | Pro | Gly | Val | Gly | Val | Pro | Gly | Val | Gly | Val | Pro | Gly | Val | Gly | Val |
|   |   |   | 260 |   |   |   |   | 265 |   |   |   |   | 270 |   |   |
| Pro | Gly | Val | Gly | Val | Pro | Gly | Val | Gly | Val | Pro | Gly | Val | Gly | Val | Pro |
|   |   | 275 |   |   |   |   | 280 |   |   |   |   | 285 |   |   |   |
| Gly | Val | Gly | Val | Pro | Gly | Val | Gly | Gly | Ala | Gly | Ala | Gly | Ser | Gly | Ala |
|   |   | 290 |   |   |   |   | 295 |   |   |   |   | 300 |   |   |   |
| Gly | Ala | Gly | Ser | Gly | Ala | Gly | Ala | Gly | Ser | Gly | Ala | Gly | Ala | Gly | Ser |
| 305 |   |   |   |   | 310 |   |   |   |   | 315 |   |   |   |   | 320 |
| Val | Pro | Gly | Val | Gly | Val | Pro | Gly | Val | Gly | Val | Pro | Gly | Val | Gly | Val |
|   |   |   |   | 325 |   |   |   |   | 330 |   |   |   |   | 335 |   |
| Pro | Gly | Val | Gly | Val | Pro | Gly | Val | Gly | Val | Pro | Gly | Val | Gly | Val | Pro |
|   |   |   | 340 |   |   |   |   | 345 |   |   |   |   | 350 |   |   |
| Gly | Val | Gly | Val | Pro | Gly | Val | Gly | Gly | Ala | Gly | Ala | Gly | Ser | Gly | Ala |
|   |   |   | 355 |   |   |   |   | 360 |   |   |   |   | 365 |   |   |
| Gly | Ala | Gly | Ser | Gly | Ala | Gly | Ala | Gly | Ser | Gly | Ala | Gly | Ala | Gly | Ser |
|   |   |   | 370 |   |   |   |   | 375 |   |   |   |   | 380 |   |   |
| Val | Pro | Gly | Val | Gly | Val | Pro | Gly | Val | Gly | Val | Pro | Gly | Val | Gly | Val |
| 385 |   |   |   |   |   | 390 |   |   |   |   | 395 |   |   |   | 400 |
| Pro | Gly | Val | Gly | Val | Pro | Gly | Val | Gly | Val | Pro | Gly | Val | Gly | Val | Pro |
|   |   |   |   | 405 |   |   |   |   | 410 |   |   |   |   | 415 |   |
| Gly | Val | Gly | Val | Pro | Gly | Val | Gly | Gly | Ala | Gly | Ala | Gly | Ser | Gly | Ala |
|   |   |   | 420 |   |   |   |   | 425 |   |   |   |   | 430 |   |   |
| Gly | Ala | Gly | Ser | Gly | Ala | Gly | Ala | Gly | Ser | Gly | Ala | Gly | Ala | Gly | Ser |
|   |   | 435 |   |   |   |   | 440 |   |   |   |   | 445 |   |   |   |
| Val | Pro | Gly | Val | Gly | Val | Pro | Gly | Val | Gly | Val | Pro | Gly | Val | Gly | Val |
|   |   | 450 |   |   |   |   | 455 |   |   |   |   | 460 |   |   |   |
| Pro | Gly | Val | Gly | Val | Pro | Gly | Val | Gly | Val | Pro | Gly | Val | Gly | Val | Pro |
| 465 |   |   |   |   | 470 |   |   |   |   | 475 |   |   |   |   | 480 |
| Gly | Val | Gly | Val | Pro | Gly | Val | Gly | Gly | Ala | Gly | Ala | Gly | Ser | Gly | Ala |
|   |   |   |   | 485 |   |   |   |   | 490 |   |   |   |   | 495 |   |
| Gly | Ala | Gly | Ser | Gly | Ala | Gly | Ala | Gly | Ser | Gly | Ala | Gly | Ala | Gly | Ser |
|   |   |   | 500 |   |   |   |   | 505 |   |   |   |   | 510 |   |   |
| Val | Pro | Gly | Val | Gly | Val | Pro | Gly | Val | Gly | Val | Pro | Gly | Val | Gly | Val |
|   |   | 515 |   |   |   |   | 520 |   |   |   |   | 525 |   |   |   |

|       |     |     |     |     |     |     |     |     |     |     |     |     |     |
|---|---|---|---|---|---|---|---|---|---|---|---|---|---|
| Pro   | Gly | Val | Gly | Val | Pro | Gly | Val | Gly | Val | Pro | Gly | Val | Pro |
|       | 530 |     |     |     | 535 |     |     |     | 540 |     |     |     |     |
| Gly   | Val | Gly | Val | Pro | Gly | Val | Gly | Ala | Gly | Ala | Gly | Ser | Gly | Ala |
| 545   |     |     |     |     | 550 |     |     |     | 555 |     |     |     | 560 |
| Gly   | Ala | Gly | Ser | Gly | Ala | Gly | Ala | Gly | Ser | Gly | Ala | Gly | Ala | Gly | Ser |
|       |     |     |     | 565 |     |     |     | 570 |     |     |     |     | 575 |
| Val   | Pro | Gly | Val | Gly | Val | Pro | Gly | Val | Gly | Val | Pro | Gly | Val | Gly | Val |
|       |     |     | 580 |     |     |     | 585 |     |     |     |     | 590 |     |
| Pro   | Gly | Val | Gly | Val | Pro | Gly | Val | Gly | Val | Pro | Gly | Val | Gly | Val | Pro |
|       |     | 595 |     |     |     | 600 |     |     |     |     | 605 |     |     |
| Gly   | Val | Gly | Val | Pro | Gly | Val | Gly | Ala | Gly | Ala | Gly | Ser | Gly | Ala |
|       | 610 |     |     |     | 615 |     |     |     | 620 |     |     |     |     |
| Gly   | Ala | Gly | Ser | Gly | Ala | Gly | Ala | Gly | Ser | Gly | Ala | Gly | Ala | Gly | Ser |
| 625   |     |     |     |     | 630 |     |     |     | 635 |     |     |     | 640 |
| Val   | Pro | Gly | Val | Gly | Val | Pro | Gly | Val | Gly | Val | Pro | Gly | Val | Gly | Val |
|       |     |     |     | 645 |     |     |     | 650 |     |     |     |     | 655 |
| Pro   | Gly | Val | Gly | Val | Pro | Gly | Val | Gly | Val | Pro | Gly | Val | Gly | Val | Pro |
|       |     |     | 660 |     |     |     | 665 |     |     |     |     | 670 |     |
| Gly   | Val | Gly | Val | Pro | Gly | Val | Gly | Ala | Gly | Ala | Gly | Ser | Gly | Ala |
|       |     | 675 |     |     |     | 680 |     |     |     |     | 685 |     |     |
| Gly   | Ala | Gly | Ser | Gly | Ala | Gly | Ala | Gly | Ser | Gly | Ala | Gly | Ala | Gly | Ser |
|       | 690 |     |     |     |     | 695 |     |     |     | 700 |     |     |     |
| Val   | Pro | Gly | Val | Gly | Val | Pro | Gly | Val | Gly | Val | Pro | Gly | Val | Gly | Val |
| 705   |     |     |     |     | 710 |     |     |     |     | 715 |     |     |     | 720 |
| Pro   | Gly | Val | Gly | Val | Pro | Gly | Val | Gly | Val | Pro | Gly | Val | Gly | Val | Pro |
|       |     |     | 725 |     |     |     | 730 |     |     |     |     | 735 |     |
| Gly   | Val | Gly | Val | Pro | Gly | Val | Gly | Ala | Gly | Ala | Gly | Ser | Gly | Ala |
|       |     |     | 740 |     |     |     | 745 |     |     |     |     | 750 |     |
| Gly   | Ala | Gly | Ser | Gly | Ala | Gly | Ala | Gly | Ser | Gly | Ala | Gly | Ala | Gly | Ser |
|       |     | 755 |     |     |     | 760 |     |     |     | 765 |     |     |     |
| Val   | Pro | Gly | Val | Gly | Val | Pro | Gly | Val | Gly | Val | Pro | Gly | Val | Gly | Val |
|       | 770 |     |     |     |     | 775 |     |     |     |     | 780 |     |     |
| Pro   | Gly | Val | Gly | Val | Pro | Gly | Val | Gly | Val | Pro | Gly | Val | Gly | Val | Pro |
| 785   |     |     |     |     | 790 |     |     |     |     | 795 |     |     |     | 800 |
| Gly   | Val | Gly | Val | Pro | Gly | Val | Gly | Ala | Gly | Ala | Gly | Ser | Gly | Ala |
|       |     |     |     | 805 |     |     |     | 810 |     |     |     |     | 815 |
| Gly   | Ala | Gly | Ser | Gly | Ala | Gly | Ala | Gly | Ser | Gly | Ala | Gly | Ala | Gly | Ser |
|       |     |     | 820 |     |     |     | 825 |     |     |     | 830 |     |     |

( 2 ) INFORMATION FOR SEQ ID NO:5:

( i ) SEQUENCE CHARACTERISTICS:
        ( A ) LENGTH: 988 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:5:

|       |     |     |     |     |     |     |     |     |     |     |     |     |     |     |
|---|---|---|---|---|---|---|---|---|---|---|---|---|---|---|
| Val   | Pro | Gly | Val | Gly | Val | Pro | Gly | Val | Gly | Val | Pro | Gly | Val | Gly | Val |
| 1     |     |     |     | 5   |     |     |     |     | 10  |     |     |     |     | 15  |
| Pro   | Gly | Val | Gly | Val | Pro | Gly | Val | Gly | Val | Pro | Gly | Val | Gly | Val | Pro |
|       |     |     | 20  |     |     |     | 25  |     |     |     |     | 30  |     |     |
| Gly   | Val | Gly | Val | Pro | Gly | Val | Gly | Ala | Gly | Ala | Gly | Ser | Gly | Ala |
|       |     | 35  |     |     |     | 40  |     |     |     |     | 45  |     |     |
| Gly   | Ala | Gly | Ser | Gly | Ala | Gly | Ala | Gly | Ser | Gly | Ala | Gly | Ala | Gly | Ser |

|  |  |  |  |  |  |  |  |  |  |  |  |  |  |  |
|---|---|---|---|---|---|---|---|---|---|---|---|---|---|---|
| | | | 50 | | | | 55 | | | | 60 | | | |
| Gly<br>65 | Ala | Gly | Ala | Gly | Ser<br>70 | Gly | Ala | Gly | Ala<br>75 | Gly | Ser | Val | Pro | Gly | Val<br>80 |
| Gly | Val | Pro | Gly | Val<br>85 | Gly | Val | Pro | Gly | Val<br>90 | Gly | Val | Pro | Gly | Val<br>95 | Gly |
| Val | Pro | Gly | Val<br>100 | Gly | Val | Pro | Gly | Val<br>105 | Gly | Val | Pro | Gly | Val<br>110 | Gly | Val |
| Pro | Gly | Val | Gly<br>115 | Gly | Ala | Gly | Ala<br>120 | Gly | Ser | Gly | Ala<br>125 | Gly | Ala | Gly | Ser |
| Gly | Ala<br>130 | Gly | Ala | Gly | Ser<br>135 | Gly | Ala | Gly | Ala<br>140 | Gly | Ser | Gly | Ala | Gly | Ala |
| Gly<br>145 | Ser | Gly | Ala | Gly | Ala<br>150 | Gly | Ser | Val | Pro<br>155 | Gly | Val | Gly | Val | Pro<br>160 | Gly |
| Val | Gly | Val | Pro | Gly<br>165 | Val | Gly | Val | Pro<br>170 | Gly | Val | Gly | Val | Pro<br>175 | Gly | Val |
| Gly | Val | Pro | Gly<br>180 | Val | Gly | Val | Pro<br>185 | Gly | Val | Gly | Val | Pro<br>190 | Gly | Val | Gly |
| Gly | Ala | Gly | Ala<br>195 | Gly | Ser | Gly | Ala<br>200 | Gly | Ala | Gly | Ser | Gly<br>205 | Ala | Gly | Ala |
| Gly | Ser<br>210 | Gly | Ala | Gly | Ala<br>215 | Gly | Ser | Gly | Ala<br>220 | Gly | Ala | Gly | Ser | Gly | Ala |
| Gly<br>225 | Ala | Gly | Ser | Val | Pro<br>230 | Gly | Val | Gly | Val<br>235 | Pro | Gly | Val | Gly | Val | Pro<br>240 |
| Gly | Val | Gly | Val | Pro<br>245 | Gly | Val | Gly | Val | Pro<br>250 | Gly | Val | Gly | Val | Pro<br>255 | Gly |
| Val | Gly | Val | Pro<br>260 | Gly | Val | Gly | Val | Pro<br>265 | Gly | Val | Gly | Gly | Ala<br>270 | Gly | Ala |
| Gly | Ser | Gly | Ala<br>275 | Gly | Ala | Gly | Ser<br>280 | Gly | Ala | Gly | Ala | Gly<br>285 | Ser | Gly | Ala |
| Gly | Ala<br>290 | Gly | Ser | Gly | Ala<br>295 | Gly | Ala | Gly | Ser<br>300 | Gly | Ala | Gly | Ala | Gly | Ser |
| Val<br>305 | Pro | Gly | Val | Gly | Val<br>310 | Pro | Gly | Val | Gly<br>315 | Val | Pro | Gly | Val | Gly | Val<br>320 |
| Pro | Gly | Val | Gly | Val<br>325 | Pro | Gly | Val | Gly | Val<br>330 | Pro | Gly | Val | Gly | Val<br>335 | Pro |
| Gly | Val | Gly | Val<br>340 | Pro | Gly | Val | Gly<br>345 | Gly | Ala | Gly | Ala | Gly<br>350 | Ser | Gly | Ala |
| Gly | Ala<br>355 | Gly | Ser | Gly | Ala<br>360 | Gly | Ala | Gly | Ser | Gly | Ala<br>365 | Gly | Ala | Gly | Ser |
| Gly | Ala<br>370 | Gly | Ala | Gly | Ser<br>375 | Gly | Ala | Gly | Ala | Gly<br>380 | Ser | Val | Pro | Gly | Val |
| Gly<br>385 | Val | Pro | Gly | Val | Gly<br>390 | Val | Pro | Gly | Val | Gly<br>395 | Val | Pro | Gly | Val | Gly<br>400 |
| Val | Pro | Gly | Val | Gly<br>405 | Val | Pro | Gly | Val | Gly<br>410 | Val | Pro | Gly | Val | Gly<br>415 | Val |
| Pro | Gly | Val | Gly<br>420 | Gly | Ala | Gly | Ala | Gly<br>425 | Ser | Gly | Ala | Gly | Ala<br>430 | Gly | Ser |
| Gly | Ala | Gly | Ala<br>435 | Gly | Ser | Gly | Ala<br>440 | Gly | Ala | Gly | Ser | Gly<br>445 | Ala | Gly | Ala |
| Gly | Ser<br>450 | Gly | Ala | Gly | Ala<br>455 | Gly | Ser | Val | Pro | Gly | Val<br>460 | Gly | Val | Pro | Gly |
| Val<br>465 | Gly | Val | Pro | Gly | Val<br>470 | Gly | Val | Pro | Gly | Val<br>475 | Gly | Val | Pro | Gly | Val<br>480 |

| | | | | | | | | | | | | | | |
|---|---|---|---|---|---|---|---|---|---|---|---|---|---|---|
| Gly | Val | Pro | Gly | Val | Gly | Val | Pro | Gly | Val | Gly | Val | Pro | Gly | Val | Gly |
| | | | | 485 | | | | 490 | | | | | | 495 | |
| Gly | Ala | Gly | Ala | Gly | Ser | Gly | Ala | Gly | Ala | Gly | Ser | Gly | Ala | Gly | Ala |
| | | | 500 | | | | | 505 | | | | | 510 | | |
| Gly | Ser | Gly | Ala | Gly | Ala | Gly | Ser | Gly | Ala | Gly | Ala | Gly | Ser | Gly | Ala |
| | | | 515 | | | | | 520 | | | | | 525 | | |
| Gly | Ala | Gly | Ser | Val | Pro | Gly | Val | Gly | Val | Pro | Gly | Val | Gly | Val | Pro |
| | | 530 | | | | 535 | | | | | 540 | | | | |
| Gly | Val | Gly | Val | Pro | Gly | Val | Gly | Val | Pro | Gly | Val | Gly | Val | Pro | Gly |
| 545 | | | | | 550 | | | | | 555 | | | | | 560 |
| Val | Gly | Val | Pro | Gly | Val | Gly | Val | Pro | Gly | Val | Gly | Gly | Ala | Gly | Ala |
| | | | | 565 | | | | | 570 | | | | | 575 | |
| Gly | Ser | Gly | Ala | Gly | Ala | Gly | Ser | Gly | Ala | Gly | Ala | Gly | Ser | Gly | Ala |
| | | | 580 | | | | | 585 | | | | | 590 | | |
| Gly | Ala | Gly | Ser | Gly | Ala | Gly | Ala | Gly | Ser | Gly | Ala | Gly | Ala | Gly | Ser |
| | | | 595 | | | | | 600 | | | | | 605 | | |
| Val | Pro | Gly | Val | Gly | Val | Pro | Gly | Val | Gly | Val | Pro | Gly | Val | Gly | Val |
| | 610 | | | | | 615 | | | | | 620 | | | | |
| Pro | Gly | Val | Gly | Val | Pro | Gly | Val | Gly | Val | Pro | Gly | Val | Gly | Val | Pro |
| 625 | | | | | 630 | | | | | 635 | | | | | 640 |
| Gly | Val | Gly | Val | Pro | Gly | Val | Gly | Gly | Ala | Gly | Ala | Gly | Ser | Gly | Ala |
| | | | | 645 | | | | | 650 | | | | | 655 | |
| Gly | Ala | Gly | Ser | Gly | Ala | Gly | Ala | Gly | Ser | Gly | Ala | Gly | Ala | Gly | Ser |
| | | | 660 | | | | | 665 | | | | | 670 | | |
| Gly | Ala | Gly | Ala | Gly | Ser | Gly | Ala | Gly | Ala | Gly | Ser | Val | Pro | Gly | Val |
| | | | 675 | | | | | 680 | | | | | 685 | | |
| Gly | Val | Pro | Gly | Val | Gly | Val | Pro | Gly | Val | Gly | Val | Pro | Gly | Val | Gly |
| | 690 | | | | | 695 | | | | | 700 | | | | |
| Val | Pro | Gly | Val | Gly | Val | Pro | Gly | Val | Gly | Val | Pro | Gly | Val | Gly | Val |
| 705 | | | | | 710 | | | | | 715 | | | | | 720 |
| Pro | Gly | Val | Gly | Gly | Ala | Gly | Ala | Gly | Ser | Gly | Ala | Gly | Ala | Gly | Ser |
| | | | | 725 | | | | | 730 | | | | | 735 | |
| Gly | Ala | Gly | Ala | Gly | Ser | Gly | Ala | Gly | Ala | Gly | Ser | Gly | Ala | Gly | Ala |
| | | | 740 | | | | | 745 | | | | | 750 | | |
| Gly | Ser | Gly | Ala | Gly | Ala | Gly | Ser | Val | Pro | Gly | Val | Gly | Val | Pro | Gly |
| | | | 755 | | | | | 760 | | | | | 765 | | |
| Val | Gly | Val | Pro | Gly | Val | Gly | Val | Pro | Gly | Val | Gly | Val | Pro | Gly | Val |
| | 770 | | | | | 775 | | | | | 780 | | | | |
| Gly | Val | Pro | Gly | Val | Gly | Val | Pro | Gly | Val | Gly | Val | Pro | Gly | Val | Gly |
| 785 | | | | | 790 | | | | | 795 | | | | | 800 |
| Gly | Ala | Gly | Ala | Gly | Ser | Gly | Ala | Gly | Ala | Gly | Ser | Gly | Ala | Gly | Ala |
| | | | | 805 | | | | | 810 | | | | | 815 | |
| Gly | Ser | Gly | Ala | Gly | Ala | Gly | Ser | Gly | Ala | Gly | Ala | Gly | Ser | Gly | Ala |
| | | | 820 | | | | | 825 | | | | | 830 | | |
| Gly | Ala | Gly | Ser | Val | Pro | Gly | Val | Gly | Val | Pro | Gly | Val | Gly | Val | Pro |
| | | 835 | | | | 840 | | | | | 845 | | | | |
| Gly | Val | Gly | Val | Pro | Gly | Val | Gly | Val | Pro | Gly | Val | Gly | Val | Pro | Gly |
| | 850 | | | | | 855 | | | | | 860 | | | | |
| Val | Gly | Val | Pro | Gly | Val | Gly | Val | Pro | Gly | Val | Gly | Gly | Ala | Gly | Ala |
| 865 | | | | | 870 | | | | | 875 | | | | | 880 |
| Gly | Ser | Gly | Ala | Gly | Ala | Gly | Ser | Gly | Ala | Gly | Ala | Gly | Ser | Gly | Ala |
| | | | | 885 | | | | | 890 | | | | | 895 | |
| Gly | Ala | Gly | Ser | Gly | Ala | Gly | Ala | Gly | Ser | Gly | Ala | Gly | Ala | Gly | Ser |
| | | | 900 | | | | | 905 | | | | | 910 | | |

|   |   |   |   |   |   |   |   |   |   |   |   |   |   |   |
|---|---|---|---|---|---|---|---|---|---|---|---|---|---|---|
| Val | Pro | Gly 915 | Val | Gly | Val | Pro | Gly 920 | Val | Gly | Val | Pro | Gly 925 | Val | Gly | Val |
| Pro | Gly 930 | Val | Gly | Val | Pro | Gly 935 | Val | Gly | Val | Pro | Gly 940 | Val | Gly | Val | Pro |
| Gly 945 | Val | Gly | Val | Pro | Gly 950 | Val | Gly | Gly | Ala | Gly 955 | Ala | Gly | Ser | Gly | Ala 960 |
| Gly | Ala | Gly | Ser | Gly 965 | Ala | Gly | Ala | Gly | Ser 970 | Gly | Ala | Gly | Ala | Gly | Ser 975 |
| Gly | Ala | Gly | Ala 980 | Gly | Ser | Gly | Ala | Gly 985 | Ala | Gly | Ser |

(2) INFORMATION FOR SEQ ID NO:6:

(i) SEQUENCE CHARACTERISTICS:
        (A) LENGTH: 1056 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:6:

|   |   |   |   |   |   |   |   |   |   |   |   |   |   |   |   |
|---|---|---|---|---|---|---|---|---|---|---|---|---|---|---|---|
| Val 1 | Pro | Gly | Val | Gly 5 | Val | Pro | Gly | Val | Gly 10 | Val | Pro | Gly | Val | Gly 15 | Val |
| Pro | Gly | Val | Gly 20 | Val | Pro | Gly | Val | Gly 25 | Val | Pro | Gly | Val | Gly 30 | Val | Pro |
| Gly | Val | Gly 35 | Val | Pro | Gly | Val | Gly 40 | Gly | Ala | Gly | Ala | Gly 45 | Ser | Gly | Ala |
| Gly | Ala | Gly | Ser 50 | Gly | Ala | Gly | Ala 55 | Gly | Ser | Gly | Ala | Gly 60 | Ala | Gly | Ser |
| Gly 65 | Ala | Gly | Ala | Gly | Ser 70 | Gly | Ala | Gly | Ala | Gly 75 | Ser | Gly | Ala | Gly | Ala 80 |
| Gly | Ser | Gly | Ala | Gly 85 | Ala | Gly | Ser | Val | Pro 90 | Gly | Val | Gly | Val | Pro 95 | Gly |
| Val | Gly | Val | Pro 100 | Gly | Val | Gly | Val | Pro 105 | Gly | Val | Gly | Val | Pro 110 | Gly | Val |
| Gly | Val | Pro 115 | Gly | Val | Gly | Val | Pro 120 | Gly | Val | Gly | Val | Pro 125 | Gly | Val | Gly |
| Gly | Ala | Gly | Ala 130 | Gly | Ser | Gly | Ala 135 | Gly | Ala | Gly | Ser 140 | Gly | Ala | Gly | Ala |
| Gly | Ser | Gly | Ala 145 | Gly | Ala | Gly | Ser 150 | Gly | Ala | Gly | Ala 155 | Gly | Ser | Gly | Ala 160 |
| Gly | Ala | Gly | Ser | Gly 165 | Ala | Gly | Ala | Gly | Ser 170 | Gly | Ala | Gly | Ala | Gly 175 | Ser |
| Val | Pro | Gly | Val 180 | Gly | Val | Pro | Gly | Val 185 | Gly | Val | Pro | Gly | Val 190 | Gly | Val |
| Pro | Gly | Val 195 | Gly | Val | Pro | Gly | Val 200 | Gly | Val | Pro | Gly | Val 205 | Gly | Val | Pro |
| Gly | Val 210 | Gly | Val | Pro | Gly | Val 215 | Gly | Gly | Ala | Gly | Ala 220 | Gly | Ser | Gly | Ala |
| Gly | Ala 225 | Gly | Ser | Gly | Ala 230 | Gly | Ala | Gly | Ser 235 | Gly | Ala | Gly | Ala | Gly | Ser 240 |
| Gly | Ala | Gly | Ala | Gly 245 | Ser | Gly | Ala | Gly | Ala 250 | Gly | Ser | Gly | Ala | Gly 255 | Ala |
| Gly | Ser | Gly | Ala 260 | Gly | Ala | Gly | Ser | Val 265 | Pro | Gly | Val | Gly | Val 270 | Pro | Gly |

```
Val  Gly  Val  Pro  Gly  Val  Gly  Val  Pro  Gly  Val  Gly  Val  Pro  Gly  Val
          275                      280                     285

Gly  Val  Pro  Gly  Val  Gly  Val  Pro  Gly  Val  Gly  Val  Pro  Gly  Val  Gly
          290                      295                     300

Gly  Ala  Gly  Ala  Gly  Ser  Gly  Ala  Gly  Ala  Gly  Ser  Gly  Ala  Gly  Ala
305                      310                     315                          320

Gly  Ser  Gly  Ala  Gly  Ala  Gly  Ser  Gly  Ala  Gly  Ala  Gly  Ser  Gly  Ala
                    325                      330                          335

Gly  Ala  Gly  Ser  Gly  Ala  Gly  Ala  Gly  Ser  Gly  Ala  Gly  Ala  Gly  Ser
               340                      345                     350

Val  Pro  Gly  Val  Gly  Val  Pro  Gly  Val  Gly  Val  Pro  Gly  Val  Gly  Val
          355                      360                     365

Pro  Gly  Val  Gly  Val  Pro  Gly  Val  Gly  Val  Pro  Gly  Val  Gly  Val  Pro
     370                      375                     380

Gly  Val  Gly  Val  Pro  Gly  Val  Gly  Gly  Ala  Gly  Ala  Gly  Ser  Gly  Ala
385                      390                     395                          400

Gly  Ala  Gly  Ser  Gly  Ala  Gly  Ala  Gly  Ser  Gly  Ala  Gly  Ala  Gly  Ser
                    405                      410                          415

Gly  Ala  Gly  Ala  Gly  Ser  Gly  Ala  Gly  Ala  Gly  Ser  Gly  Ala  Gly  Ala
               420                      425                     430

Gly  Ser  Gly  Ala  Gly  Ala  Gly  Ser  Val  Pro  Gly  Val  Gly  Val  Pro  Gly
          435                      440                     445

Val  Gly  Val  Pro  Gly  Val  Gly  Val  Pro  Gly  Val  Gly  Val  Pro  Gly  Val
     450                      455                     460

Gly  Val  Pro  Gly  Val  Gly  Val  Pro  Gly  Val  Gly  Val  Pro  Gly  Val  Gly
465                      470                     475                          480

Gly  Ala  Gly  Ala  Gly  Ser  Gly  Ala  Gly  Ala  Gly  Ser  Gly  Ala  Gly  Ala
                    485                      490                          495

Gly  Ser  Gly  Ala  Gly  Ala  Gly  Ser  Gly  Ala  Gly  Ala  Gly  Ser  Gly  Ala
               500                      505                     510

Gly  Ala  Gly  Ser  Gly  Ala  Gly  Ala  Gly  Ser  Gly  Ala  Gly  Ala  Gly  Ser
          515                      520                     525

Val  Pro  Gly  Val  Gly  Val  Pro  Gly  Val  Gly  Val  Pro  Gly  Val  Gly  Val
     530                      535                     540

Pro  Gly  Val  Gly  Val  Pro  Gly  Val  Gly  Val  Pro  Gly  Val  Gly  Val  Pro
545                      550                     555                          560

Gly  Val  Gly  Val  Pro  Gly  Val  Gly  Gly  Ala  Gly  Ala  Gly  Ser  Gly  Ala
                    565                      570                          575

Gly  Ala  Gly  Ser  Gly  Ala  Gly  Ala  Gly  Ser  Gly  Ala  Gly  Ala  Gly  Ser
               580                      585                     590

Gly  Ala  Gly  Ala  Gly  Ser  Gly  Ala  Gly  Ala  Gly  Ser  Gly  Ala  Gly  Ala
          595                      600                     605

Gly  Ser  Gly  Ala  Gly  Ala  Gly  Ser  Val  Pro  Gly  Val  Gly  Val  Pro  Gly
     610                      615                     620

Val  Gly  Val  Pro  Gly  Val  Gly  Val  Pro  Gly  Val  Gly  Val  Pro  Gly  Val
625                      630                     635                          640

Gly  Val  Pro  Gly  Val  Gly  Val  Pro  Gly  Val  Gly  Val  Pro  Gly  Val  Gly
                    645                      650                          655

Gly  Ala  Gly  Ala  Gly  Ser  Gly  Ala  Gly  Ala  Gly  Ser  Gly  Ala  Gly  Ala
               660                      665                     670

Gly  Ser  Gly  Ala  Gly  Ala  Gly  Ser  Gly  Ala  Gly  Ala  Gly  Ser  Gly  Ala
          675                      680                     685

Gly  Ala  Gly  Ser  Gly  Ala  Gly  Ala  Gly  Ser  Gly  Ala  Gly  Ala  Gly  Ser
     690                      695                     700
```

| Val | Pro | Gly | Val | Gly | Val | Pro | Gly | Val | Gly | Val | Pro | Gly | Val | Gly | Val |
| 705 | | | | 710 | | | | | 715 | | | | | | 720 |

| Pro | Gly | Val | Gly | Val | Pro | Gly | Val | Gly | Val | Pro | Gly | Val | Gly | Val | Pro |
| | | | | 725 | | | | | 730 | | | | | 735 | |

| Gly | Val | Gly | Val | Pro | Gly | Val | Gly | Gly | Ala | Gly | Ala | Gly | Ser | Gly | Ala |
| | | | 740 | | | | | 745 | | | | | 750 | | |

| Gly | Ala | Gly | Ser | Gly | Ala | Gly | Ala | Gly | Ser | Gly | Ala | Gly | Ala | Gly | Ser |
| | | 755 | | | | | 760 | | | | | | 765 | | |

| Gly | Ala | Gly | Ala | Gly | Ser | Gly | Ala | Gly | Ala | Gly | Ser | Gly | Ala | Gly | Ala |
| | | 770 | | | | | 775 | | | | | | 780 | | |

| Gly | Ser | Gly | Ala | Gly | Ala | Gly | Ser | Val | Pro | Gly | Val | Gly | Val | Pro | Gly |
| 785 | | | | | 790 | | | | | 795 | | | | | 800 |

| Val | Gly | Val | Pro | Gly | Val | Gly | Val | Pro | Gly | Val | Gly | Val | Pro | Gly | Val |
| | | | | 805 | | | | | 810 | | | | | 815 | |

| Gly | Val | Pro | Gly | Val | Gly | Val | Pro | Gly | Val | Gly | Val | Pro | Gly | Val | Gly |
| | | | 820 | | | | | 825 | | | | | 830 | | |

| Gly | Ala | Gly | Ala | Gly | Ser | Gly | Ala | Gly | Ala | Gly | Ser | Gly | Ala | Gly | Ala |
| | | 835 | | | | | 840 | | | | | | 845 | | |

| Gly | Ser | Gly | Ala | Gly | Ala | Gly | Ser | Gly | Ala | Gly | Ala | Gly | Ser | Gly | Ala |
| 850 | | | | | 855 | | | | | | 860 | | | | |

| Gly | Ala | Gly | Ser | Gly | Ala | Gly | Ala | Gly | Ser | Gly | Ala | Gly | Ala | Gly | Ser |
| 865 | | | | | 870 | | | | | 875 | | | | | 880 |

| Val | Pro | Gly | Val | Gly | Val | Pro | Gly | Val | Gly | Val | Pro | Gly | Val | Gly | Val |
| | | | | 885 | | | | | 890 | | | | | 895 | |

| Pro | Gly | Val | Gly | Val | Pro | Gly | Val | Gly | Val | Pro | Gly | Val | Gly | Val | Pro |
| | | | 900 | | | | | 905 | | | | | 910 | | |

| Gly | Val | Gly | Val | Pro | Gly | Val | Gly | Gly | Ala | Gly | Ala | Gly | Ser | Gly | Ala |
| | | 915 | | | | | 920 | | | | | | 925 | | |

| Gly | Ala | Gly | Ser | Gly | Ala | Gly | Ala | Gly | Ser | Gly | Ala | Gly | Ala | Gly | Ser |
| 930 | | | | | 935 | | | | | 940 | | | | | |

| Gly | Ala | Gly | Ala | Gly | Ser | Gly | Ala | Gly | Ala | Gly | Ser | Gly | Ala | Gly | Ala |
| 945 | | | | | 950 | | | | | 955 | | | | | 960 |

| Gly | Ser | Gly | Ala | Gly | Ala | Gly | Ser | Val | Pro | Gly | Val | Gly | Val | Pro | Gly |
| | | | | 965 | | | | | 970 | | | | | 975 | |

| Val | Gly | Val | Pro | Gly | Val | Gly | Val | Pro | Gly | Val | Gly | Val | Pro | Gly | Val |
| | | | 980 | | | | | 985 | | | | | 990 | | |

| Gly | Val | Pro | Gly | Val | Gly | Val | Pro | Gly | Val | Gly | Val | Pro | Gly | Val | Gly |
| | | 995 | | | | | 1000 | | | | | 1005 | | | |

| Gly | Ala | Gly | Ala | Gly | Ser | Gly | Ala | Gly | Ala | Gly | Ser | Gly | Ala | Gly | Ala |
| | | 1010 | | | | | 1015 | | | | | 1020 | | | |

| Gly | Ser | Gly | Ala | Gly | Ala | Gly | Ser | Gly | Ala | Gly | Ala | Gly | Ser | Gly | Ala |
| 1025 | | | | | 1030 | | | | | 1035 | | | | | 1040 |

| Gly | Ala | Gly | Ser | Gly | Ala | Gly | Ala | Gly | Ser | Gly | Ala | Gly | Ala | Gly | Ser |
| | | | | 1045 | | | | | 1050 | | | | | 1055 | |

( 2 ) INFORMATION FOR SEQ ID NO:7:

( i ) SEQUENCE CHARACTERISTICS:
        ( A ) LENGTH: 972 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:7:

```
Val  Pro  Gly  Val  Gly  Val  Pro  Gly  Val  Gly  Val  Pro  Gly  Val  Gly  Val
 1                  5                   10                      15

Pro  Gly  Val  Gly  Val  Pro  Gly  Val  Gly  Val  Pro  Gly  Val  Gly  Val  Pro
               20                   25                      30

Gly  Val  Gly  Val  Pro  Gly  Val  Gly  Val  Pro  Gly  Val  Gly  Val  Pro  Gly
          35                       40                       45

Val  Gly  Val  Pro  Gly  Val  Gly  Val  Pro  Gly  Val  Gly  Gly  Ala  Gly  Ala
     50                       55                       60

Gly  Ser  Gly  Ala  Gly  Ala  Gly  Ser  Gly  Ala  Gly  Ala  Gly  Ser  Gly  Ala
65                       70                       75                        80

Gly  Ala  Gly  Ser  Gly  Ala  Gly  Ala  Gly  Ser  Gly  Ala  Gly  Ala  Gly  Ser
                85                        90                        95

Gly  Ala  Gly  Ala  Gly  Ser  Gly  Ala  Gly  Ala  Gly  Ser  Val  Pro  Gly  Val
               100                      105                     110

Gly  Val  Pro  Gly  Val  Gly  Val  Pro  Gly  Val  Gly  Val  Pro  Gly  Val  Gly
               115                      120                     125

Val  Pro  Gly  Val  Gly  Val  Pro  Gly  Val  Gly  Val  Pro  Gly  Val  Gly  Val
     130                      135                     140

Pro  Gly  Val  Gly  Val  Pro  Gly  Val  Gly  Val  Pro  Gly  Val  Gly  Val  Pro
145                      150                     155                      160

Gly  Val  Gly  Val  Pro  Gly  Val  Gly  Gly  Ala  Gly  Ser  Gly  Ala  Gly  Ala
               165                     170                     175

Gly  Ala  Gly  Ser  Gly  Ala  Gly  Ala  Gly  Ser  Gly  Ala  Gly  Ala  Gly  Ser
               180                     185                     190

Gly  Ala  Gly  Ala  Gly  Ser  Gly  Ala  Gly  Ala  Gly  Ser  Gly  Ala  Gly  Ala
               195                     200                     205

Gly  Ser  Gly  Ala  Gly  Ala  Gly  Ser  Val  Pro  Gly  Val  Gly  Val  Pro  Gly
210                      215                     220

Val  Gly  Val  Pro  Gly  Val  Gly  Val  Pro  Gly  Val  Gly  Val  Pro  Gly  Val
225                      230                     235                      240

Gly  Val  Pro  Gly  Val  Gly  Val  Pro  Gly  Val  Gly  Val  Pro  Gly  Val  Gly
               245                     250                     255

Val  Pro  Gly  Val  Gly  Val  Pro  Gly  Val  Gly  Val  Pro  Gly  Val  Gly  Val
               260                     265                     270

Pro  Gly  Val  Gly  Gly  Ala  Gly  Ala  Gly  Ser  Gly  Ala  Gly  Ala  Gly  Ser
          275                     280                     285

Gly  Ala  Gly  Ala  Gly  Ser  Gly  Ala  Gly  Ala  Gly  Ser  Gly  Ala  Gly  Ala
          290                     295                     300

Gly  Ser  Gly  Ala  Gly  Ala  Gly  Ser  Gly  Ala  Gly  Ala  Gly  Ser  Gly  Ala
305                      310                     315                      320

Gly  Ala  Gly  Ser  Val  Pro  Gly  Val  Gly  Val  Pro  Gly  Val  Gly  Val  Pro
               325                     330                     335

Gly  Val  Gly  Val  Pro  Gly  Val  Gly  Val  Pro  Gly  Val  Gly  Val  Pro  Gly
          340                     345                     350

Val  Gly  Val  Pro  Gly  Val  Gly  Val  Pro  Gly  Val  Gly  Val  Pro  Gly  Val
          355                     360                     365

Gly  Val  Pro  Gly  Val  Gly  Val  Pro  Gly  Val  Gly  Val  Pro  Gly  Val  Gly
          370                     375                     380

Gly  Ala  Gly  Ala  Gly  Ser  Gly  Ala  Gly  Ala  Gly  Ser  Gly  Ala  Gly  Ala
385                      390                     395                      400

Gly  Ser  Gly  Ala  Gly  Ala  Gly  Ser  Gly  Ala  Gly  Ala  Gly  Ser  Gly  Ala
               405                     410                     415

Gly  Ala  Gly  Ser  Gly  Ala  Gly  Ala  Gly  Ser  Gly  Ala  Gly  Ala  Gly  Ser
               420                     425                     430
```

| | | | | | | | | | | | | | | |
|---|---|---|---|---|---|---|---|---|---|---|---|---|---|---|
| Val | Pro | Gly | Val | Gly | Val | Pro | Gly | Val | Gly | Val | Pro | Gly | Val | Gly | Val |
| | | 435 | | | | 440 | | | | 445 | | | | | |
| Pro | Gly | Val | Gly | Val | Pro | Gly | Val | Gly | Val | Pro | Gly | Val | Gly | Val | Pro |
| | 450 | | | | 455 | | | | 460 | | | | | | |
| Gly | Val | Gly | Val | Pro | Gly | Val | Gly | Val | Pro | Gly | Val | Gly | Val | Pro | Gly |
| 465 | | | | 470 | | | | 475 | | | | | | | 480 |
| Val | Gly | Val | Pro | Gly | Val | Gly | Val | Pro | Gly | Val | Gly | Gly | Ala | Gly | Ala |
| | | | 485 | | | | | 490 | | | | | | 495 | |
| Gly | Ser | Gly | Ala | Gly | Ala | Gly | Ser | Gly | Ala | Gly | Ala | Gly | Ser | Gly | Ala |
| | | | 500 | | | | 505 | | | | | 510 | | | |
| Gly | Ala | Gly | Ser | Gly | Ala | Gly | Ala | Gly | Ser | Gly | Ala | Gly | Ala | Gly | Ser |
| | | 515 | | | | 520 | | | | | 525 | | | | |
| Gly | Ala | Gly | Ala | Gly | Ser | Gly | Ala | Gly | Ala | Gly | Ser | Val | Pro | Gly | Val |
| | 530 | | | | 535 | | | | | 540 | | | | | |
| Gly | Val | Pro | Gly | Val | Gly | Val | Pro | Gly | Val | Gly | Val | Pro | Gly | Val | Gly |
| 545 | | | | | 550 | | | | 555 | | | | | | 560 |
| Val | Pro | Gly | Val | Gly | Val | Pro | Gly | Val | Gly | Val | Pro | Gly | Val | Gly | Val |
| | | | | 565 | | | | 570 | | | | | | 575 | |
| Pro | Gly | Val | Gly | Val | Pro | Gly | Val | Gly | Val | Pro | Gly | Val | Gly | Val | Pro |
| | | | 580 | | | | | 585 | | | | | 590 | | |
| Gly | Val | Gly | Val | Pro | Gly | Val | Gly | Gly | Ala | Gly | Ala | Gly | Ser | Gly | Ala |
| | | 595 | | | | | 600 | | | | | 605 | | | |
| Gly | Ala | Gly | Ser | Gly | Ala | Gly | Ala | Gly | Ser | Gly | Ala | Gly | Ala | Gly | Ser |
| | 610 | | | | | 615 | | | | | 620 | | | | |
| Gly | Ala | Gly | Ala | Gly | Ser | Gly | Ala | Gly | Ala | Gly | Ser | Gly | Ala | Gly | Ala |
| 625 | | | | | 630 | | | | | 635 | | | | | 640 |
| Gly | Ser | Gly | Ala | Gly | Ala | Gly | Ser | Val | Pro | Gly | Val | Gly | Val | Pro | Gly |
| | | | | 645 | | | | | 650 | | | | | 655 | |
| Val | Gly | Val | Pro | Gly | Val | Gly | Val | Pro | Gly | Val | Gly | Val | Pro | Gly | Val |
| | | | 660 | | | | | 665 | | | | | 670 | | |
| Gly | Val | Pro | Gly | Val | Gly | Val | Pro | Gly | Val | Gly | Val | Pro | Gly | Val | Gly |
| | | 675 | | | | | 680 | | | | | 685 | | | |
| Val | Pro | Gly | Val | Gly | Val | Pro | Gly | Val | Gly | Val | Pro | Gly | Val | Gly | Val |
| | 690 | | | | | 695 | | | | | 700 | | | | |
| Pro | Gly | Val | Gly | Gly | Ala | Gly | Ala | Gly | Ser | Gly | Ala | Gly | Ala | Gly | Ser |
| 705 | | | | | 710 | | | | 715 | | | | | | 720 |
| Gly | Ala | Gly | Ala | Gly | Ser | Gly | Ala | Gly | Ala | Gly | Ser | Gly | Ala | Gly | Ala |
| | | | | 725 | | | | | 730 | | | | | 735 | |
| Gly | Ser | Gly | Ala | Gly | Ala | Gly | Ser | Gly | Ala | Gly | Ala | Gly | Ser | Gly | Ala |
| | | | 740 | | | | | 745 | | | | | 750 | | |
| Gly | Ala | Gly | Ser | Val | Pro | Gly | Val | Gly | Val | Pro | Gly | Val | Gly | Val | Pro |
| | | 755 | | | | | 760 | | | | | 765 | | | |
| Gly | Val | Gly | Val | Pro | Gly | Val | Gly | Val | Pro | Gly | Val | Gly | Val | Pro | Gly |
| | 770 | | | | | 775 | | | | | 780 | | | | |
| Val | Gly | Val | Pro | Gly | Val | Gly | Val | Pro | Gly | Val | Gly | Val | Pro | Gly | Val |
| 785 | | | | | 790 | | | | | 795 | | | | | 800 |
| Gly | Val | Pro | Gly | Val | Gly | Val | Pro | Gly | Val | Gly | Val | Pro | Gly | Val | Gly |
| | | | | 805 | | | | | 810 | | | | | 815 | |
| Gly | Ala | Gly | Ala | Gly | Ser | Gly | Ala | Gly | Ala | Gly | Ser | Gly | Ala | Gly | Ala |
| | | | 820 | | | | | 825 | | | | | 830 | | |
| Gly | Ser | Gly | Ala | Gly | Ala | Gly | Ser | Gly | Ala | Gly | Ala | Gly | Ser | Gly | Ala |
| | | 835 | | | | | 840 | | | | | 845 | | | |
| Gly | Ala | Gly | Ser | Gly | Ala | Gly | Ala | Gly | Ser | Gly | Ala | Gly | Ala | Gly | Ser |

|   |   |   |   |   | 850 |   |   |   |   | 855 |   |   |   |   | 860 |   |   |
|---|---|---|---|---|---|---|---|---|---|---|---|---|---|---|---|---|---|

Val Pro Gly Val Gly Val Pro Gly Val Gly Val Pro Gly Val Gly Val
865                     870                     875                     880

Pro Gly Val Gly Val Pro Gly Val Gly Val Pro Gly Val Gly Val Pro
                    885                     890                     895

Gly Val Gly Val Pro Gly Val Gly Val Pro Gly Val Gly Val Pro Gly
                900                     905                     910

Val Gly Val Pro Gly Val Gly Val Pro Gly Val Gly Gly Ala Gly Ala
            915                     920                     925

Gly Ser Gly Ala Gly Ala Gly Ser Gly Ala Gly Ala Gly Ser Gly Ala
930                     935                     940

Gly Ala Gly Ser Gly Ala Gly Ala Gly Ser Gly Ala Gly Ala Gly Ser
945                     950                     955                     960

Gly Ala Gly Ala Gly Ser Gly Ala Gly Ala Gly Ser
                    965                     970

( 2 ) INFORMATION FOR SEQ ID NO:8:

( i ) SEQUENCE CHARACTERISTICS:
        ( A ) LENGTH: 1024 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:8:

Val Pro Gly Val Gly Val Pro Gly Val Gly Val Pro Gly Val Gly Val
1               5                       10                      15

Pro Gly Val Gly Val Pro Gly Val Gly Val Pro Gly Val Gly Val Pro
            20                      25                      30

Gly Val Gly Val Pro Gly Val Gly Val Pro Gly Val Gly Val Pro Gly
        35                      40                      45

Val Gly Val Pro Gly Val Gly Val Pro Gly Val Gly Val Pro Gly Val
    50                      55                      60

Gly Val Pro Gly Val Gly Val Pro Gly Val Gly Val Pro Gly Val Gly
65                      70                      75                      80

Gly Ala Gly Ala Gly Ser Gly Ala Gly Ala Gly Ser Gly Ala Gly Ala
                85                      90                      95

Gly Ser Gly Ala Gly Ala Gly Ser Gly Ala Gly Ala Gly Ser Gly Ala
            100                     105                     110

Gly Ala Gly Ser Gly Ala Gly Ala Gly Ser Gly Ala Gly Ala Gly Ser
        115                     120                     125

Val Pro Gly Val Gly Val Pro Gly Val Gly Val Pro Gly Val Gly Val
    130                     135                     140

Pro Gly Val Gly Val Pro Gly Val Gly Val Pro Gly Val Gly Val Pro
145                     150                     155                     160

Gly Val Gly Val Pro Gly Val Gly Val Pro Gly Val Gly Val Pro Gly
                165                     170                     175

Val Gly Val Pro Gly Val Gly Val Pro Gly Val Gly Val Pro Gly Val
            180                     185                     190

Gly Val Pro Gly Val Gly Val Pro Gly Val Gly Val Pro Gly Val Gly
        195                     200                     205

Gly Ala Gly Ala Gly Ser Gly Ala Gly Ala Gly Ser Gly Ala Gly Ala
    210                     215                     220

Gly Ser Gly Ala Gly Ala Gly Ser Gly Ala Gly Ala Gly Ser Gly Ala
225                     230                     235                     240

```
Gly Ala Gly Ser Gly Ala Gly Ala Gly Ser Gly Ala Gly Ala Gly Ser
                245                 250                 255
Val Pro Gly Val Gly Val Pro Gly Val Gly Val Pro Gly Val Gly Val
            260             265             270
Pro Gly Val Gly Val Pro Gly Val Gly Val Pro Gly Val Gly Val Pro
        275             280             285
Gly Val Gly Val Pro Gly Val Gly Val Pro Gly Val Gly Val Pro Gly
    290             295             300
Val Gly Val Pro Gly Val Gly Val Pro Gly Val Gly Val Pro Gly Val
305             310             315                             320
Gly Val Pro Gly Val Gly Val Pro Gly Val Gly Val Pro Gly Val Gly
            325             330                             335
Gly Ala Gly Ala Gly Ser Gly Ala Gly Ala Gly Ser Gly Ala Gly Ala
            340             345             350
Gly Ser Gly Ala Gly Ala Gly Ser Gly Ala Gly Ala Gly Ser Gly Ala
        355             360             365
Gly Ala Gly Ser Gly Ala Gly Ala Gly Ser Gly Ala Gly Ala Gly Ser
        370             375             380
Val Pro Gly Val Gly Val Pro Gly Val Gly Val Pro Gly Val Gly Val
385             390             395                             400
Pro Gly Val Gly Val Pro Gly Val Gly Val Pro Gly Val Gly Val Pro
            405             410             415
Gly Val Gly Val Pro Gly Val Gly Val Pro Gly Val Gly Val Pro Gly
            420             425             430
Val Gly Val Pro Gly Val Gly Val Pro Gly Val Gly Val Pro Gly Val
            435             440             445
Gly Val Pro Gly Val Gly Val Pro Gly Val Gly Val Pro Gly Val Gly
    450             455             460
Gly Ala Gly Ala Gly Ser Gly Ala Gly Ala Gly Ser Gly Ala Gly Ala
465             470             475                             480
Gly Ser Gly Ala Gly Ala Gly Ser Gly Ala Gly Ala Gly Ser Gly Ala
            485             490                             495
Gly Ala Gly Ser Gly Ala Gly Ala Gly Ser Gly Ala Gly Ala Gly Ser
            500             505             510
Val Pro Gly Val Gly Val Pro Gly Val Gly Val Pro Gly Val Gly Val
            515             520             525
Pro Gly Val Gly Val Pro Gly Val Gly Val Pro Gly Val Gly Val Pro
    530             535             540
Gly Val Gly Val Pro Gly Val Gly Val Pro Gly Val Gly Val Pro Gly
545             550             555                             560
Val Gly Val Pro Gly Val Gly Val Pro Gly Val Gly Val Pro Gly Val
            565             570                             575
Gly Val Pro Gly Val Gly Val Pro Gly Val Gly Val Pro Gly Val Gly
            580             585                             590
Gly Ala Gly Ala Gly Ser Gly Ala Gly Ala Gly Ser Gly Ala Gly Ala
            595             600                             605
Gly Ser Gly Ala Gly Ala Gly Ser Gly Ala Gly Ala Gly Ser Gly Ala
        610             615             620
Gly Ala Gly Ser Gly Ala Gly Ala Gly Ser Gly Ala Gly Ala Gly Ser
625             630             635                             640
Val Pro Gly Val Gly Val Pro Gly Val Gly Val Pro Gly Val Gly Val
            645             650                             655
Pro Gly Val Gly Val Pro Gly Val Gly Val Pro Gly Val Gly Val Pro
```

|   |   |   | 660 |   |   |   |   | 665 |   |   |   |   | 670 |   |   |
|---|---|---|---|---|---|---|---|---|---|---|---|---|---|---|---|

Gly Val Gly Val Pro Gly Val Gly Val Pro Gly Val Gly Val Pro Gly
        675                 680                 685

Val Gly Val Pro Gly Val Gly Val Pro Gly Val Gly Val Pro Gly Val
    690                 695                 700

Gly Val Pro Gly Val Gly Val Pro Gly Val Gly Val Pro Gly Val Gly
705                 710                 715                 720

Gly Ala Gly Ala Gly Ser Gly Ala Gly Ala Gly Ser Gly Ala Gly Ala
                725                 730                 735

Gly Ser Gly Ala Gly Ala Gly Ser Gly Ala Gly Ala Gly Ser Gly Ala
            740                 745                 750

Gly Ala Gly Ser Gly Ala Gly Ala Gly Ser Gly Ala Gly Ala Gly Ser
        755                 760                 765

Val Pro Gly Val Gly Val Pro Gly Val Gly Val Pro Gly Val Gly Val
    770                 775                 780

Pro Gly Val Gly Val Pro Gly Val Gly Val Pro Gly Val Gly Val Pro
785                 790                 795                 800

Gly Val Gly Val Pro Gly Val Gly Val Pro Gly Val Gly Val Pro Gly
                805                 810                 815

Val Gly Val Pro Gly Val Gly Val Pro Gly Val Gly Val Pro Gly Val
            820                 825                 830

Gly Val Pro Gly Val Gly Val Pro Gly Val Gly Val Pro Gly Val Gly
        835                 840                 845

Gly Ala Gly Ala Gly Ser Gly Ala Gly Ala Gly Ser Gly Ala Gly Ala
    850                 855                 860

Gly Ser Gly Ala Gly Ala Gly Ser Gly Ala Gly Ala Gly Ser Gly Ala
865                 870                 875                 880

Gly Ala Gly Ser Gly Ala Gly Ala Gly Ser Gly Ala Gly Ala Gly Ser
                885                 890                 895

Val Pro Gly Val Gly Val Pro Gly Val Gly Val Pro Gly Val Gly Val
            900                 905                 910

Pro Gly Val Gly Val Pro Gly Val Gly Val Pro Gly Val Gly Val Pro
        915                 920                 925

Gly Val Gly Val Pro Gly Val Gly Val Pro Gly Val Gly Val Pro Gly
    930                 935                 940

Val Gly Val Pro Gly Val Gly Val Pro Gly Val Gly Val Pro Gly Val
945                 950                 955                 960

Gly Val Pro Gly Val Gly Val Pro Gly Val Gly Val Pro Gly Val Gly
                965                 970                 975

Gly Ala Gly Ala Gly Ser Gly Ala Gly Ala Gly Ser Gly Ala Gly Ala
            980                 985                 990

Gly Ser Gly Ala Gly Ala Gly Ser Gly Ala Gly Ala Gly Ser Gly Ala
        995                 1000                1005

Gly Ala Gly Ser Gly Ala Gly Ala Gly Ser Gly Ala Gly Ala Gly Ser
    1010                1015                1020

( 2 ) INFORMATION FOR SEQ ID NO:9:

( i ) SEQUENCE CHARACTERISTICS:
        ( A ) LENGTH: 208 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:9:

-continued

| | | | | | | | | | | | | | | |
|---|---|---|---|---|---|---|---|---|---|---|---|---|---|---|
| Val 1 | Pro | Gly | Val | Gly 5 | Val | Pro | Gly | Val 10 | Gly | Val | Pro | Gly | Val | Gly 15 | Val |
| Pro | Gly | Val | Gly 20 | Val | Pro | Gly | Val | Gly 25 | Val | Pro | Gly | Val | Gly 30 | Val | Pro |
| Gly | Val | Gly 35 | Val | Pro | Gly | Val | Gly 40 | Val | Pro | Gly | Val | Gly 45 | Val | Pro | Gly |
| Val | Gly 50 | Val | Pro | Gly | Val | Gly 55 | Val | Pro | Gly | Val | Gly 60 | Val | Pro | Gly | Val |
| Gly 65 | Val | Pro | Gly | Val | Gly 70 | Val | Pro | Gly | Val | Gly 75 | Val | Pro | Gly | Val | Gly 80 |
| Val | Pro | Gly | Val | Gly 85 | Val | Pro | Gly | Val | Gly 90 | Val | Pro | Gly | Val | Gly 95 | Val |
| Pro | Gly | Val | Gly 100 | Val | Pro | Gly | Val | Gly 105 | Val | Pro | Gly | Val | Gly 110 | Val | Pro |
| Gly | Val | Gly 115 | Val | Pro | Gly | Val | Gly 120 | Val | Pro | Gly | Val | Gly 125 | Val | Pro | Gly |
| Val | Gly 130 | Val | Pro | Gly | Val | Gly 135 | Val | Pro | Gly | Val | Gly 140 | Val | Pro | Gly | Val |
| Gly 145 | Val | Pro | Gly | Val | Gly 150 | Val | Pro | Gly | Val | Gly 155 | Val | Pro | Gly | Val | Gly 160 |
| Gly | Ala | Gly | Ala | Gly 165 | Ser | Gly | Ala | Gly 170 | Ala | Gly | Ser | Gly | Ala | Gly 175 | Ala |
| Gly | Ser | Gly | Ala 180 | Gly | Ala | Gly | Ser | Gly 185 | Ala | Gly | Ala | Gly | Ser 190 | Gly | Ala |
| Gly | Ala | Gly 195 | Ser | Gly | Ala | Gly | Ala 200 | Gly | Ser | Gly | Ala | Gly 205 | Ala | Gly | Ser |